US012692234B2

(12) United States Patent
Kopczynski et al.

(10) Patent No.: US 12,692,234 B2
(45) Date of Patent: Jul. 28, 2026

(54) ROCK INHIBITORS AND USES THEREOF

(71) Applicant: Alcon Inc., Fribourg (CH)

(72) Inventors: Casey Casimir Kopczynski, Chapel Hill, NC (US); Jill Marie Sturdivant, Chapel Hill, NC (US); Michael Scott McClure, Cary, NC (US); Anjali Biren Joshi, Cary, NC (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 19/253,364

(22) Filed: Jun. 27, 2025

(65) Prior Publication Data

US 2026/0001848 A1 Jan. 1, 2026

Related U.S. Application Data

(60) Provisional application No. 63/666,009, filed on Jun. 28, 2024.

(51) Int. Cl.

| | |
|---|---|
| ***C07D 217/02*** | (2006.01) |
| ***A61K 9/00*** | (2006.01) |
| ***A61K 31/472*** | (2006.01) |
| ***A61K 31/5575*** | (2006.01) |
| ***A61K 47/02*** | (2006.01) |
| ***A61K 47/18*** | (2017.01) |
| ***A61K 47/26*** | (2006.01) |
| ***A61P 27/06*** | (2006.01) |
| ***A61P 27/14*** | (2006.01) |

(52) U.S. Cl.

CPC .......... *C07D 217/02* (2013.01); *A61K 9/0048* (2013.01); *A61K 31/472* (2013.01); *A61K 31/5575* (2013.01); *A61K 47/02* (2013.01); *A61K 47/186* (2013.01); *A61K 47/26* (2013.01); *A61P 27/06* (2018.01); *A61P 27/14* (2018.01)

(58) Field of Classification Search

CPC ........ C07D 217/02; A61P 27/06; A61P 27/14; A61K 9/0048

See application file for complete search history.

(56) References Cited

U.S. PATENT DOCUMENTS

| | | | | |
|---|---|---|---|---|
| 8,394,826 | B2 | 3/2013 | deLong et al. | |
| 10,550,087 | B2 | 2/2020 | Sturdivant et al. | |
| 2020/0002324 | A1 | 1/2020 | deLong et al. | |
| 2021/0363141 | A1* | 11/2021 | deLong | A61P 1/18 |

OTHER PUBLICATIONS

Bastin et al. (Organic Process Research and Development (2000) 4:427-435). (Year: 2000).*

Chemical Abstract Sen/ice, Columbus, Ohio, US; Nov. 23, 2010 (Nov. 23, 2010), XP093309905, Database accession No. 1254032-45-5.

Sturdivant, Jill M, et al. "Discovery of the ROCK inhibitor netarsudil for the treatment of open-angle glaucoma." Bioorganic & medicinal chemistry letters 26.10 (2016): 2475-2480.

Bastin, Richard J. et al.. "Salt selection and optimisation procedures for pharmaceutical new chemical entities." Organic Process Research & Development 4.5 (2000): 427-435.

Berge, S. M. "Pharmaceutical Salts Journal of Pharmaceutical Sciences, vol. 66." (1977): 1-19.

Caira, Mino R. "Crystalline polymorphism of organic compounds." Topics in Current Chemistry. Springer Berlin Heidelberg, 1999. vol. 198, (1998): 163-208, XPO01156954, ISSN: 0340-1022, DOI: 10.1007/3-540-69178-2_5.

International Search Report and Written Opinion, mailed Sep. 12, 2025, for International Application No. PCT/IB2025/056590 filed on Jun. 28, 2025.

DeLong et al., "Asymmetric Synthesis of Netarsudil: A New Therapeutic for Open-Angle Glaucoma", Synthesis 51(04), 2018, pp. 953-959.

* cited by examiner

*Primary Examiner* — Marcos L Sznaidman

(74) *Attorney, Agent, or Firm* — K&L Gates LLP; Brian J. Novak; Benjamin D. Heuberger

(57) ABSTRACT

Provided herein are compounds comprising a formula of 4-(3-amino-1-(isoquinolin-6-ylamino)-1-oxopropan-2-yl) benzyl adamantane carboxylate (e.g., compounds of formula (I) or formula (II)) or a pharmaceutically acceptable salt thereof. The compounds are useful for reducing intraocular pressure and for treating glaucoma or ocular hypertension.

3 Claims, 18 Drawing Sheets

B

C

D

1

C 1

B

4

E → 3

3 → 4

ROCK INHIBITORS AND USES THEREOF

RELATED APPLICATIONS

This application claims priority of U.S. Provisional Patent Application No. 63/666,009, filed Jun. 28, 2024, the entire content of which is incorporated herein by reference.

BACKGROUND

Sensory perception via the five senses of hearing, vision, taste, smell, and touch serves as a bridge for human interpretation and interaction with the world. Loss or damage to any one of these senses poses significant challenges to an affected individual's daily existence. Vision, for example, is naturally possible because of the brain centrally processing sensory stimuli received by an eye and transmitted to the brain via an optic nerve. Damage to an otherwise functional optic nerve, which leads to reduced or terminated vision, is to be avoided if possible. One way in which the optic nerve becomes damaged is via compression resulting from acute or chronic increased intraocular pressure, which can present clinically as a variety of diagnosable outcomes, including glaucomas (e.g., primary open-angle glaucoma or angle-closure glaucoma) or ocular hypertension.

Several medications have been developed and are currently in use to mitigate elevated intraocular pressure and prevent damage to the optic nerve, thereby treating glaucoma. Ocular instillation of medications used in managing glaucoma decrease eye pressure by improving drainage of eye fluid, decreasing the amount of fluid made by the eye, or both. Drugs to treat glaucoma may be classified by their active ingredient and include alpha agonists, beta blockers, carbonic anhydrase inhibitors, cholinergics, prostaglandin analogs, and rho kinase inhibitors, as well as combination therapies.

Alpha agonists, including brimonidine and apraclonidine, work to both decrease production of fluid and increase drainage, but present side effects that can include burning or stinging upon instillation of the eye drop, fatigue, headache, drowsiness, dry mouth, and dry nose.

Beta blockers, including levobunolol, timolol, and betaxolol, work by decreasing production of intraocular fluid, but present side effects that can include low blood pressure, reduced pulse rate, and fatigue.

Carbonic anhydrase inhibitors (CAIs), including acetazolamide, methazolamide, dorzolamide, and brinzolamide, reduce eye pressure by decreasing the production of intraocular fluid, but present side effects that include stinging, burning and other eye discomfort.

Cholinergic (miotic) medications, including pilocarpine and carbachol, reduce eye pressure by increasing the drainage of intraocular fluid through the trabecular meshwork, but present with side effects that include dim vision, especially at night or in darkened areas such as movie theaters.

Prostaglandin analogs, including bimatoprost, travoprost, latanoprost, and tafluprost, work by increasing the outflow of intraocular fluid from the eye. They have few systemic side effects but present with side effects that can include eye color change, growth of eyelashes, darkening of eyelid skin, eyelash growth, droopy eyelids, sunken eyes, stinging, eye redness, and itching.

Inhibitors of Rho-associated protein kinases, including ripasudil and netarsudil, increase drainage of intraocular fluid by improving outflow through the trabecular meshwork, but present with side effects that can include eye redness (e.g., conjunctival hyperemia), corneal deposits, stinging, and small bleeds on the white of the eye.

Combined medications, including brinzolamide with brimonidine, netarsudil with latanoprost, brimonidine with timolol, and dorzolomide with timolol, work by increasing drainage of intraocular fluid and/or reducing the production of fluid, but present with side effects that include eye redness and stinging (netarsudil with latanoprost), the symptoms of beta blockers and alpha agonists (brimonidine and timolol), burning or stinging of the eyes and changes in sense of taste (dorzolomide with timolol), and blurred vision, eye irritation, bad taste, dry mouth, and eye allergy (brinzolamide and brimonidine).

Side effects of medications may affect patient compliance with their prescribed therapeutic regimen (skipping dosages or discontinuation of therapy), and thereby inhibit the otherwise beneficial clinical result of such medication. Side effects also present a barrier to commercial adoption, at least, because physicians may be reluctant to prescribe a therapy due to its known side effects notwithstanding efficacy, even superior efficacy, of the therapy. Thus, there is a need for improved ocular therapeutics, which may include, among other advantages, reduced side effects, improved efficacy, or both.

SUMMARY

Provided herein are compounds having a formula:

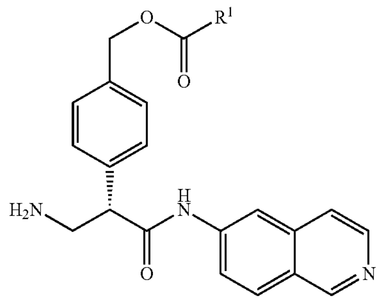

or a pharmaceutically acceptable salt thereof, wherein $R^1$ is adamantanyl (e.g., 1-adamantanyl or 2-adamantanyl), which may be optionally substituted with one or more substituents selected, independently from halogen (e.g., F or Br), methyl, ethyl, propyl, or isopropyl.

Also provided herein are methods of administration, comprising ocular instillation of a compound or composition described herein.

Also provided herein are methods of treating glaucoma (e.g., primary open-angle glaucoma or angle-closure glaucoma) in a subject in need thereof, comprising administration of a compound or composition described herein to the subject.

Also provided herein are methods of treating ocular hypertension in a subject in need thereof, comprising administration of a compound or composition described herein to the subject.

Also provided herein are methods of reducing intraocular pressure in a subject in need thereof, comprising administration of a compound or composition described herein to the subject.

Also provided herein are methods of inhibiting a Rho-associated protein kinase (ROCK), comprising contacting the ROCK with a compound or composition described herein.

DETAILED DESCRIPTION

Figure 1:
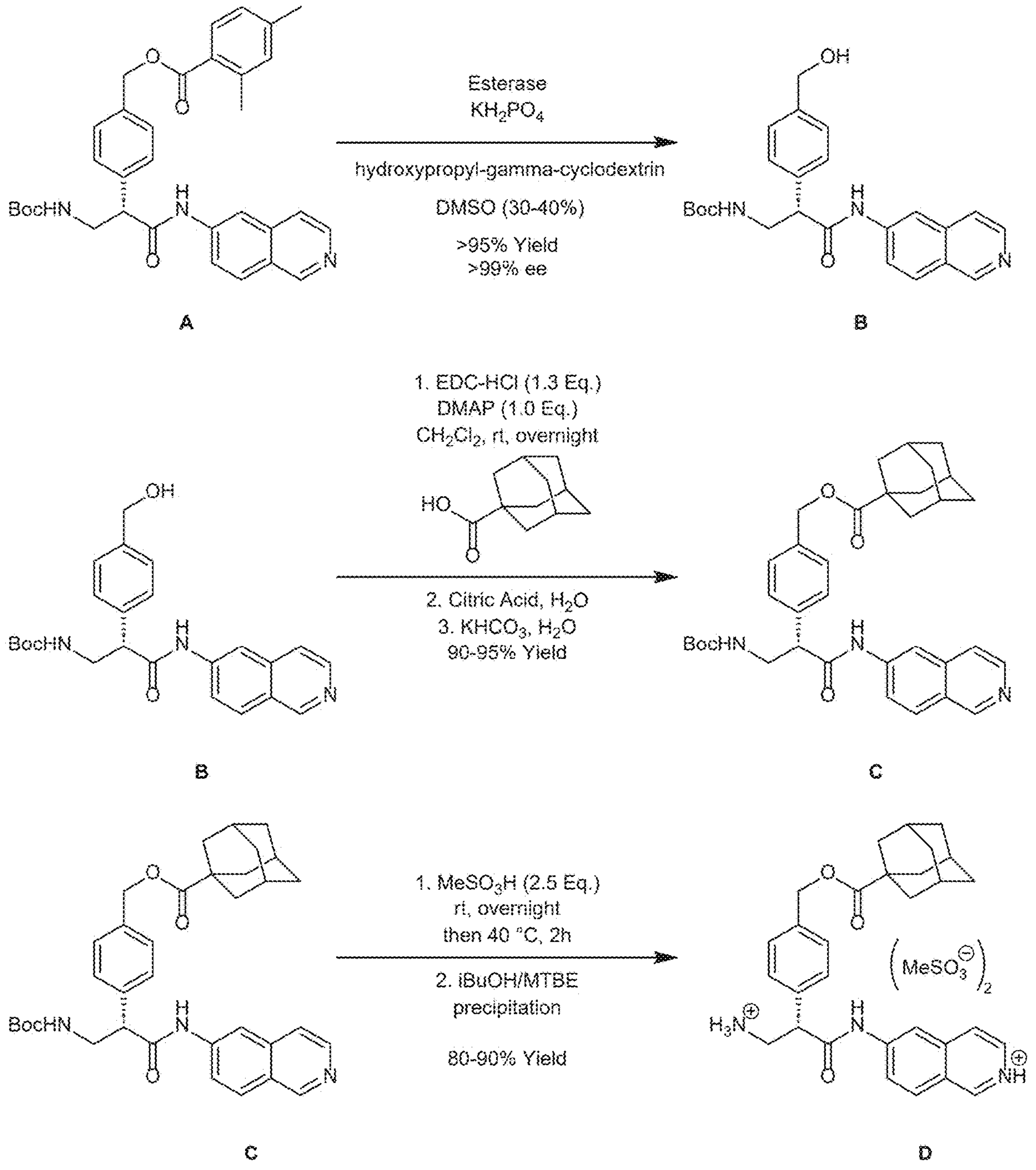
FIG. 1 depicts a synthetic scheme for preparing Compound B from Compound A, Compound C from Compound B, and Compound D from Compound C.

Glaucoma, the leading cause of irreversible blindness worldwide, is a chronic and progressive optic neuropathy characterized by damage to the optic and retinal nerve fiber layers, which can lead to permanent loss of peripheral or central vision. Reduction of intraocular pressure (IOP) is the only known modifiable risk factor for preventing and treating glaucoma. As explained above, several therapeutic classes have been utilized to impart intraocular pressure reduction. One class includes inhibitors of Rho-associated protein kinases (ROCK), such as ripasudil and netarsudil.

ROCK inhibitors are a class of glaucoma drugs with a distinct mechanism of action and generally good safety profile. They act on the trabecular tissue, increase the outflow of aqueous humor, and reduce intraocular pressure. Elevated intraocular pressure (IOP) is an established risk factor for progression of glaucoma (e.g., primary open-angle glaucoma or angle-closure glaucoma) (see Douglas J. Rhee, "Overview of Glaucoma," Merck Manual, volume 225 March 2025 (merckmanuals.com/professional/eye-disorders/glaucoma/overview-of-glaucoma)).

Rho is a 200-300 amino acid-long intracellular signal transduction protein that is activated when coupled with guanosine diphosphate (GDP). Rho-associated protein kinases (ROCK) are a group of 160-kDa serine/threonine protein kinases. Activated Rho binds to and activates ROCK, which phosphorylates downstream intracellular substrates. Classical substrates include myosin light chain (MLC), myosin phosphatase substrate 1 (MYPT1), kinase C-potentiated phosphatase inhibitor 17 (CP1-17), LIM kinase (LIMK), calmodulin (CaM), ezrin, radixin, and moesin. Binding of ROCK to these substrates may regulate myosin/actin contraction, cell morphology, stiffness, adhesion, and matrix synthesis. The two subtypes, ROCK1 and ROCK2, are homologous, but differ in tissue distribution and function. ROCK1 is mainly expressed in non-neural tissues, such as the heart, lung, and skeletal muscle, whereas ROCK2 is mainly expressed in the brain. Both subtypes are expressed in the eye, but not in the lens.

Notwithstanding ocular therapeutic benefits of ROCK inhibition, ROCK inhibitors (ROCK1) can also cause local adverse reactions, including common conjunctival hyperemia (eye redness) and subconjunctival bleeding. For example, ocular instillation of ripasudil and netarsudil can present with mild to severe hyperemia in over half of patients. Without wishing to be bound by theory, it is thought that netarsudil can elicit hyperemia for up to 24 hours because the compound is maintained in the cornea prior to hydrolysis via corneal esterase activity. Both netarsudil and its esterase hydrolysed metabolite ((S)-3-amino-2-(4-(hydroxymethyl)phenyl)-N-(isoquinolin-6-yl) propenamide; Compound 3) exhibit potent ROCK1 activity, but only the metabolite is released into the eye to reach its target tissue, the trabecular meshwork. Until such hydrolysis occurs, it is thought, without being limited by theory, that the netarsudil depot in the cornea can diffuse back into the tear film continuing to effect conjunctival hyperemia.

Surprisingly, it has been found that the compounds herein exhibit 9-fold poorer ROCK2i activity than netarsudil yet provide similar or better intraocular pressure reduction and simultaneously reduce concurrent side effects such as hyperemia compared to netarsudil alone or a fixed dose combination of netarsudil with latanoprost.

DEFINITIONS

Certain terms, whether used alone or as part of a phrase or another term, are defined below.

The articles "a" and "an" refer to one or to more than one of the grammatical object of the article.

Numerical values relating to measurements are subject to measurement errors that place limits on their accuracy. For this reason, the term "about" may explicitly or implicitly modify all numerical values provided herein, unless otherwise indicated.

The term "about" generally indicates a possible variation of a numerical value. In some embodiments, the possible variation (±) may be no more than 10%, 5%, or 1% of the numerical value. In some embodiments, the last decimal place of a numerical value provided herein indicates its degree of accuracy. In some embodiments, where no other error margins are given, the maximum margin is ascertained by applying the rounding-off convention to the last decimal place or last significant digit when a decimal is not present in the given numerical value.

The term "amelioration" means a lessening of severity of at least one indicator of a condition or disease, such as a delay or slowing in the progression of one or more indicators of a condition or disease. The severity of indicators may be determined by subjective or objective measures which are known to those skilled in the art.

The terms "composition" and "pharmaceutical composition" refer to a mixture of at least one compound described herein with another component, such as a carrier or a pharmaceutically acceptable carrier, respectively, and/or optionally another pharmaceutically active compound. The pharmaceutical composition facilitates administration of the compound to a patient or subject. Multiple techniques of administering a composition exist including, but not limited to, ocular instillation, or intravenous, oral, nasal, rectal, intravaginal, aerosol, parenteral, buccal, sublingual, ophthalmic, pulmonary, transdermal, and topical administration.

The terms "effective amount" and "therapeutically effective amount" refer to an amount of therapeutic compound, such as a compound described herein, administered to a subject, either as a single dose or as part of a series of doses, which is effective to produce a desired therapeutic effect.

The term "pharmaceutically acceptable carrier" means a pharmaceutically acceptable material, composition, or carrier, such as a liquid filler, solid filler, stabilizer, dispersing agent, suspending agent, diluent, excipient, thickening agent, solvent, or encapsulating material, involved in carrying or transporting at least one compound described herein within or to the patient such that the compound may perform its intended function. A given carrier must be "acceptable" in the sense of being compatible with the other ingredients of a particular formulation, including the compounds described herein, and not injurious to the patient. Other ingredients that may be included in the pharmaceutical compositions or dosage forms described herein are known in the art and described, for example, in "Remington's Pharmaceutical Sciences" (Genaro (Ed.), Mack Publishing Co., 1985), the entire content of which is incorporated herein by reference.

The term "pharmaceutically acceptable salt" refers to derivatives of the disclosed compounds wherein the parent compound is modified by converting an existing acid or base moiety to its salt form. Lists of salts are found in "Handbook of Pharmaceutical Salts: Properties, Selection, and Use" (P. Henrich Stahl & Camille G. Wermuth (Eds.), VHCA & Wiley-VCH, 2002), the entire content of which is incorporated herein by reference.

The terms "treatment" or "treating" refer to the application of one or more specific procedures used for the amelioration of a disease. The term "treatment" can include "therapeutic treatment". A "prophylactic" treatment, refers to reducing the rate of progression of the disease or condition being treated, delaying the onset of that disease or condition, or reducing the severity of its onset.

Recitation of ranges of values herein is merely intended to serve as a shorthand method of referring individually to each separate value falling within the range. Unless otherwise indicated herein, each individual value is incorporated into the specification as if it were individually recited herein. All methods described herein may be performed in any suitable order, and may include a combination of one or more embodiments herein, unless otherwise indicated herein or otherwise clearly contradicted by context. The use of examples, or exemplary language ("for example," "such as," etc.) provided herein is intended merely to better illuminate the described subject matter and does not pose a limitation on the scope of the subject matter otherwise claimed. No language in the specification should be construed as indicating any non-claimed element essential to practicing the described subject matter.

Each group member of a grouping of alternative elements or embodiments of this disclosure may be referred to and claimed individually or in any combination with other members of the group or other elements found herein. Furthermore, a recited member of a group may be included in, or excluded from, another recited group for reasons of convenience or patentability.

Reference made to a patent or printed publication document throughout this specification incorporate herein by reference the document's entire content.

Embodiments of this disclosure are illustrative. Accordingly, the present disclosure is not limited to that precisely as shown and described.

Compounds

Provided herein are compounds having a formula (I):

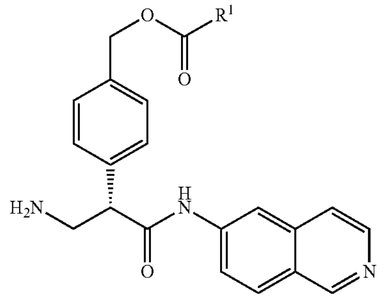

or a pharmaceutically acceptable salt thereof, wherein $R^1$ is adamantanyl (e.g., 1-adamantanyl or 2-adamantanyl), which may be optionally substituted with one or more substituents selected, independently from halogen (e.g., F or Br), methyl, ethyl, propyl, or isopropyl.

Also provided herein are compounds having a formula (II):

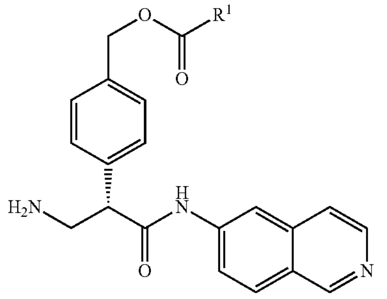

or a pharmaceutically acceptable salt, other than hydrochloride, thereof, wherein $R^1$ is adamantanyl (e.g., 1-adamantanyl or 2-adamantanyl), which may be optionally substituted with one or more substituents selected, independently from halogen (e.g., F or Br), methyl, ethyl, propyl, or isopropyl.

In some embodiments, the compound of the formula is 4-((S)-3-amino-1-(isoquinolin-6-ylamino)-1-oxopropan-2-yl)benzyl adamantane-1-carboxylate (Compound 1), or a pharmaceutically acceptable salt thereof. In some embodiments, the compound of the formula is a monomesylate, dimesylate, monohydrochloride, dihydrochloride, tosylate, maleate, fumarate, or citrate salt of the compound, e.g., of 4-((S)-3-amino-1-(isoquinolin-6-ylamino)-1-oxopropan-2-yl)benzyl adamantane-1-carboxylate. In some embodiments, the compound of the formula is a dimesylate salt of 4-((S)-3-amino-1-(isoquinolin-6-ylamino)-1-oxopropan-2-yl)benzyl adamantane-1-carboxylate. In some embodiments, the compound of the formula is a monomesylate salt of 4-((S)-3-amino-1-(isoquinolin-6-ylamino)-1-oxopropan-2-yl)benzyl adamantane-1-carboxylate. In some embodiments, the compound of the formula is 4-((S)-3-amino-1-(isoquinolin-6-ylamino)-1-oxopropan-2-yl)benzyl adamantane-1-carboxylate.

In some embodiments, the compound of the formula is 4-((S)-3-amino-1-(isoquinolin-6-ylamino)-1-oxopropan-2-yl)benzyl adamantane-2-carboxylate (Compound 2), or a pharmaceutically acceptable salt thereof. In some embodiments, the compound of the formula is a monomesylate, dimesylate, monohydrochloride, dihydrochloride, tosylate, maleate, fumarate, or citrate salt of 4-((S)-3-amino-1-(isoquinolin-6-ylamino)-1-oxopropan-2-yl)benzyl adamantane-2-carboxylate. In some embodiments, the compound of the formula is a dimesylate salt of 4-((S)-3-amino-1-(isoquinolin-6-ylamino)-1-oxopropan-2-yl)benzyl adamantane-2-carboxylate. In some embodiments, the compound of the formula is a monomesylate salt of 4-((S)-3-amino-1-(isoquinolin-6-ylamino)-1-oxopropan-2-yl)benzyl adamantane-2-carboxylate. In some embodiments, the compound of the formula is 4-((S)-3-amino-1-(isoquinolin-6-ylamino)-1-oxopropan-2-yl)benzyl adamantane-2-carboxylate.

In some embodiments, the adamantane carboxylate compounds herein are provided as a solid form. In some embodiments, the solid form is an amorphous solid form. In some embodiments, the solid form is a co-crystal solid form. In some embodiments, the solid form is selected from:

- a solid form of 4-((S)-3-amino-1-(isoquinolin-6-ylamino)-1-oxopropan-2-yl)benzyl adamantane-1-carboxylate having a melting point range of about 80 to about 87° C.;
- a solid form of a monomesylate salt of 4-((S)-3-amino-1-(isoquinolin-6-ylamino)-1-oxopropan-2-yl)benzyl adamantane-1-carboxylate having a melting point range of about 166 to about 170° C.;
- a solid form of a dimesylate salt of 4-((S)-3-amino-1-(isoquinolin-6-ylamino)-1-oxopropan-2-yl)benzyl adamantane-1-carboxylate having a melting point range of about 160 to about 165° C.;
- a solid form of a monohydrochloride salt of 4-((S)-3-amino-1-(isoquinolin-6-ylamino)-1-oxopropan-2-yl)benzyl adamantane-1-carboxylate having a melting point range of about 157 to about 158° C.;
- a solid form of a dihydrochloride salt of 4-((S)-3-amino-1-(isoquinolin-6-ylamino)-1-oxopropan-2-yl)benzyl adamantane-1-carboxylate having a melting point range of about 215 to about 222° C.;
- a solid form of a tosylate salt of 4-((S)-3-amino-1-(isoquinolin-6-ylamino)-1-oxopropan-2-yl)benzyl adamantane-1-carboxylate having a melting point range of about 205 to about 210° C.;
- a solid form of a maleate salt of 4-((S)-3-amino-1-(isoquinolin-6-ylamino)-1-oxopropan-2-yl)benzyl adamantane-1-carboxylate having a melting point range of about 162 to about 169
- a solid form of a fumarate salt of 4-((S)-3-amino-1-(isoquinolin-6-ylamino)-1-oxopropan-2-yl)benzyl adamantane-1-carboxylate having a melting point range of about 180 to about 184° C.; or
- a solid form of a citrate salt of 4-((S)-3-amino-1-(isoquinolin-6-ylamino)-1-oxopropan-2-yl)benzyl adamantane-1-carboxylate having a melting point range of about 173 to about 176° C.

Compound 1 and Compound 2 are depicted in structural form below.
Compound 1
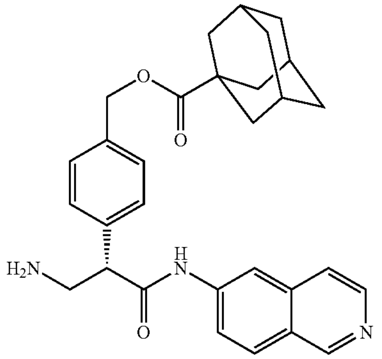
Compound 2
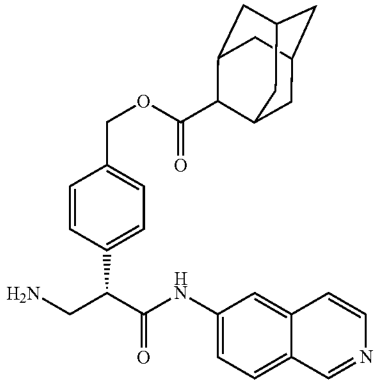
Compound 3 (metabolite of Netarsudil) and Compound 4 are depicted in structural form below.
Compound 3
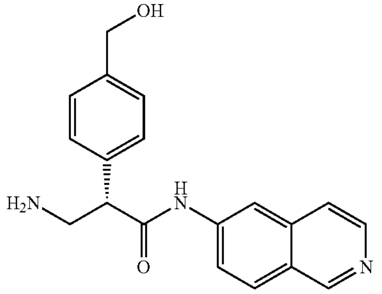
Compound 4
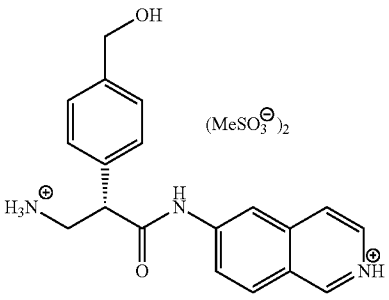
Compound A and Compound B are depicted in structural form below.
Compound A
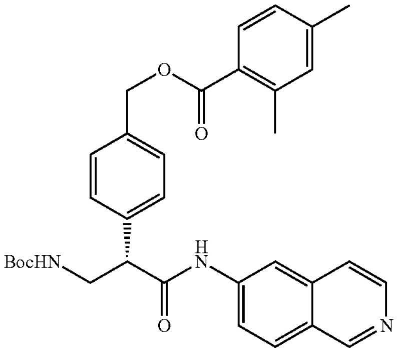
Compound B
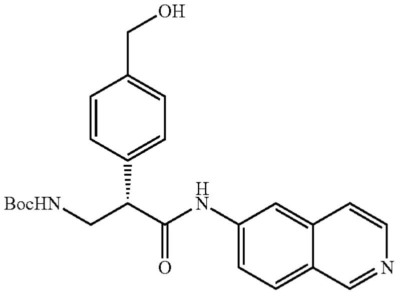
Compound C and Compound D are depicted in structural form below.
Compound C
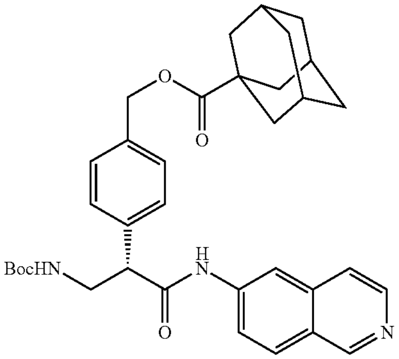
Compound D
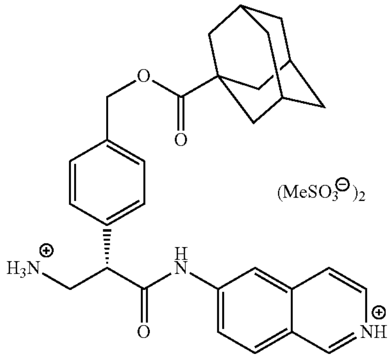

Netarsudil and Compound E are depicted in structural form below.

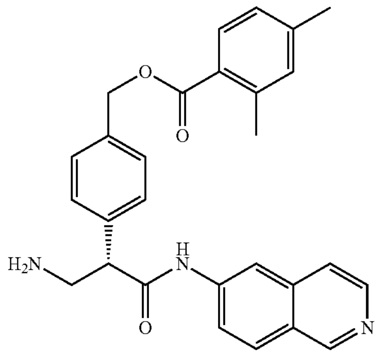

Netarsudi

Compound E

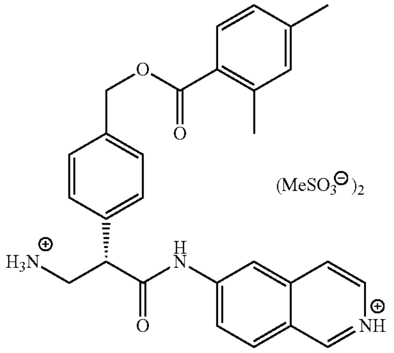

Compound 1 monomesylate (mono-methanesulfonate) and Compound 2 monomesylate are depicted in structural form below.

Compound 1 monomesylate

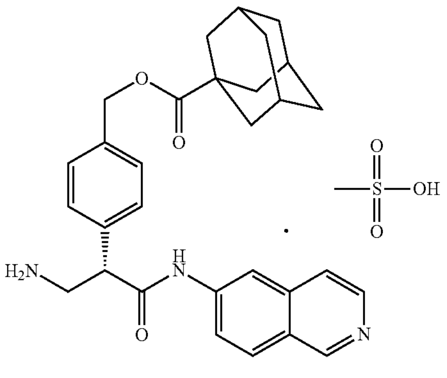

-continued

Compound 2 monomesylate

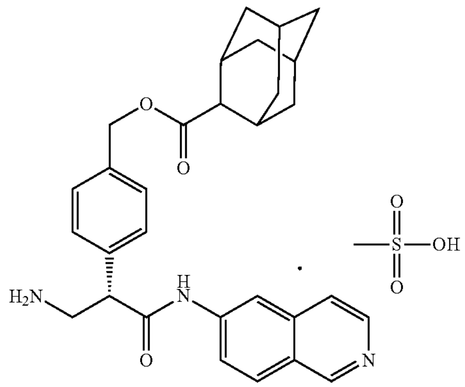

Also provided herein are synthetic intermediate compounds useful in methods for preparing the above compounds (including, but not limited to, Compound 1, Compound 2, Compound D (a dimesylate salt of Compound 1), a monomesylate salt of Compound 1, a dimesylate salt of Compound 2, or a monomesylate salt of Compound 2), the synthetic intermediate compounds having a formula (III):

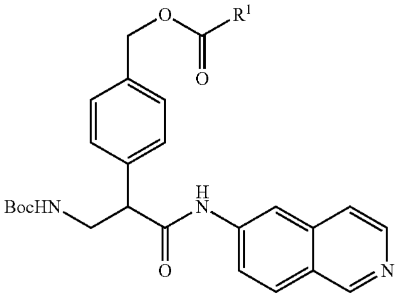

or a pharmaceutically acceptable salt thereof, wherein $R^1$ is adamantanyl (e.g., 1-adamantanyl or 2-adamantanyl), which may be optionally substituted with one or more substituents selected, independently from halogen (e.g., F or Br), methyl, ethyl, propyl, or isopropyl.

Also provided herein are synthetic intermediate compounds useful in methods for preparing the above compounds (including, but not limited to, Compound 1, Compound 2, Compound D (a dimesylate salt of Compound 1), a monomesylate salt of Compound 1, a dimesylate salt of Compound 2, or a monomesylate salt of Compound 2), the synthetic intermediate compounds having a formula (IV):

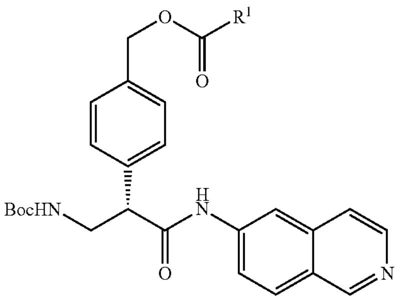

or a pharmaceutically acceptable salt thereof, wherein $R^1$ is adamantanyl (e.g., 1-adamantanyl or 2-adamantanyl), which may be optionally substituted with one or more substituents selected, independently from halogen (e.g., F or Br), methyl, ethyl, propyl, or isopropyl. In some embodiments, the synthetic intermediate compound is Compound C.

The present disclosure also includes isotopically-labeled compounds, which are identical to those recited in the formulae herein (e.g., Compound 1 and Compound 2), but for the fact that one or more atoms are replaced by an atom having an atomic mass or mass number abundance different from the atomic mass or mass number abundance usually found in nature. Examples of isotopes suitable for inclusion in the compounds of this invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}p$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example, increased in vivo half-life or reduced dosage requirements and hence may be preferred in some circumstances. The compound may incorporate positron-emitting isotopes for medical imaging and positron-emitting tomography (PET) studies for determining the distribution of receptors. Suitable positron-emitting isotopes that can be incorporated in the compounds herein are $^{11}C$, $^{13}N$, $^{15}O$, and $^{18}F$. Compounds herein that are isotopically-labeled can generally be prepared by conventional techniques known to those skilled in the art or by processes analogous to those described herein using appropriate isotopically-labeled reagents or starting materials in place of non-isotopically-labeled reagents or starting materials.

The disclosed compounds may exist as pharmaceutically acceptable salts. The term "pharmaceutically acceptable salt" refers to salts or zwitterions of the compounds that are suitable for therapeutic use without undue toxicity, irritation, or allergic response, commensurate with a reasonable benefit/risk ratio and effective for their intended use. The salts may be prepared during the final isolation and purification of the compounds or separately by reacting, for example, an amino group of the compounds with a suitable acid. For example, a compound may be dissolved in a suitable solvent, such as, but not limited to, methanol and water and treated with at least one equivalent of an acid, like hydrochloric acid. The resulting salt may then precipitate and be isolated by filtration and dried under reduced pressure. Alternatively, the solvent and any excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of an acidic group (e.g., a carboxyl group) with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Synthesis

Compounds herein may be prepared analogous to synthetic methods described in U.S. Pat. No. 8,394,826, for example, regarding compounds E139, E145, and E175 therein, or US20210094918A1, or analogous to the synthetic methods of deLong and Sturdivant, Synthesis 2019, 51, 953-959, the entire content of each of which is hereby incorporated by reference. Additionally, compounds herein may be prepared according to the Examples below and the synthetic schemes depicted in FIG. 1, FIG. 2, FIG. 3, FIG. 4., FIG. 13, and FIG. 14. While the synthetic schemes depicted in the figures and Examples herein show compounds having stereochemistry, the corresponding racemic compounds may be prepared according to analogous synthetic schemes.

In some embodiments, Compound A ((S)-4-(3-((tert-butoxycarbonyl)amino)-1-(isoquinolin-6-ylamino)-1-oxopropan-2-yl)benzyl 2,4-dimethylbenzoate) as depicted in FIG. 1 may be prepared according to the synthetic methods described in U.S. Pat. No. 8,394,826 regarding compound E145 therein. In some embodiments, Compound A can be prepared as described in U.S. Pat. No. 10,550,087 regarding compound 3 therein, the entire content of which is hereby incorporated by reference.

In some embodiments, Compound B (tert-butyl(S)-(2-(4-(hydroxymethyl)phenyl)-3-(isoquinolin-6-ylamino)-3-oxopropyl) carbamate) as depicted in FIG. 1 may be prepared according to the synthetic methods described in U.S. Pat. No. 8,394,826 regarding compound E139 therein, the entire content of which is hereby incorporated by reference.

In some embodiments, Compound A may be converted to Compound B as depicted in the synthetic method of FIG. 1.

In some embodiments, Compound B may be converted to Compound C (4-((S)-3-((tert-butoxycarbonyl)amino)-1-(isoquinolin-6-ylamino)-1-oxopropan-2-yl)benzyl adamantane-1-carboxylate) as depicted in the synthetic method of FIG. 1.

Figure 2:
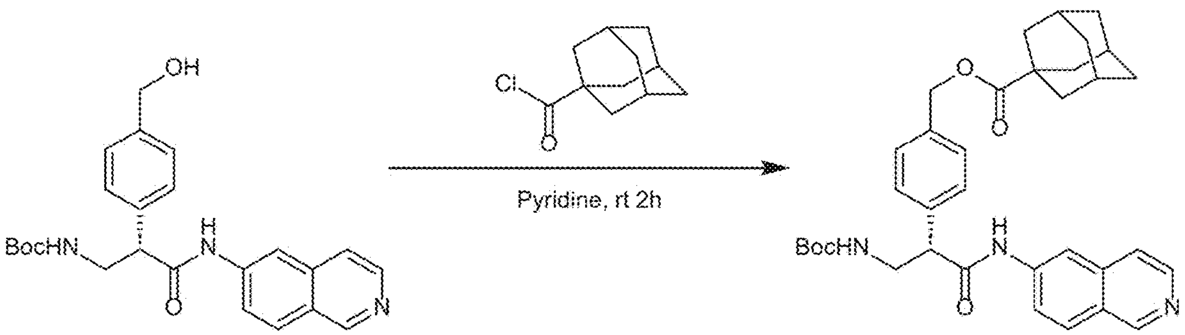
FIG. 2 depicts another synthetic scheme for preparing Compound C from Compound B.

In some embodiments, Compound B may be converted to Compound C as depicted in the synthetic method of FIG. 2; formula (I) or formula (II) may be similarly prepared using the corresponding adamantane carboxylic acid.

In some embodiments, Compound C may be converted to Compound D (a dimesylate salt of 4-((S)-3-amino-1-(isoquinolin-6-ylamino)-1-oxopropan-2-yl)benzyl adamantane-1-carboxylate) as depicted in FIG. 1; a dimesylate salt of formula (I) or formula (II) being similarly prepared from either formula (III) or formula (IV). The corresponding monomesylate may be similarly prepared. In some embodiments, other mono- or di-salts referred to herein may be prepared analogously by replacing methanesulfonic acid with the corresponding acid to provide the desired di-salt. In some embodiments, other mono- or di-salts referred to herein may also be prepared by treating a solution of Compound 1 in a solvent with at least 1 or 2 molar equivalents of the corresponding acid followed by isolation of the mono- or di-salt of Compound 1, or formula (I), or formula (II).

Figure 3:
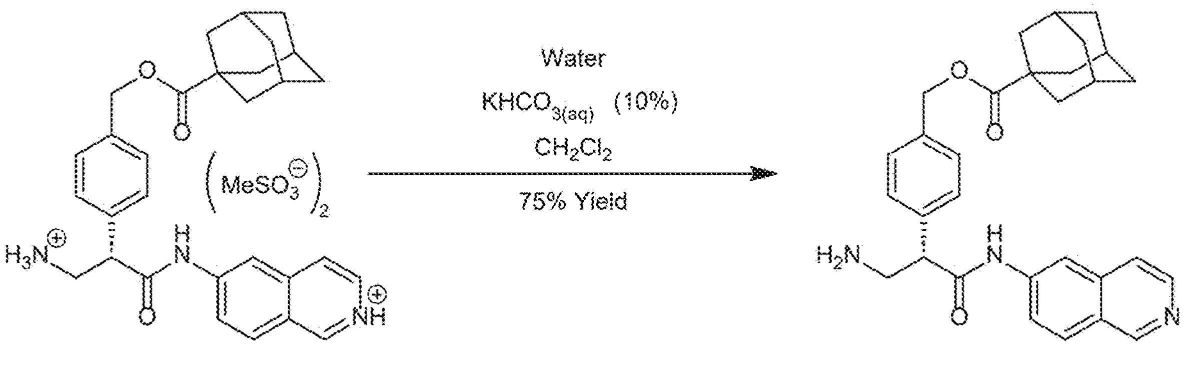
FIG. 3 depicts a synthetic scheme for preparing Compound 1 from Compound D.

In some embodiments, Compound 1 (4-((S)-3-amino-1-(isoquinolin-6-ylamino)-1-oxopropan-2-yl)benzyl adamantane-1-carboxylate) may be prepared by treatment of Compound D with an aqueous solution of $KHCO_3$ in dichloromethane as depicted in FIG. 3; formula (I) or formula (II) may be similarly prepared from a salt of either formula (III) or formula (IV).

Figure 4:
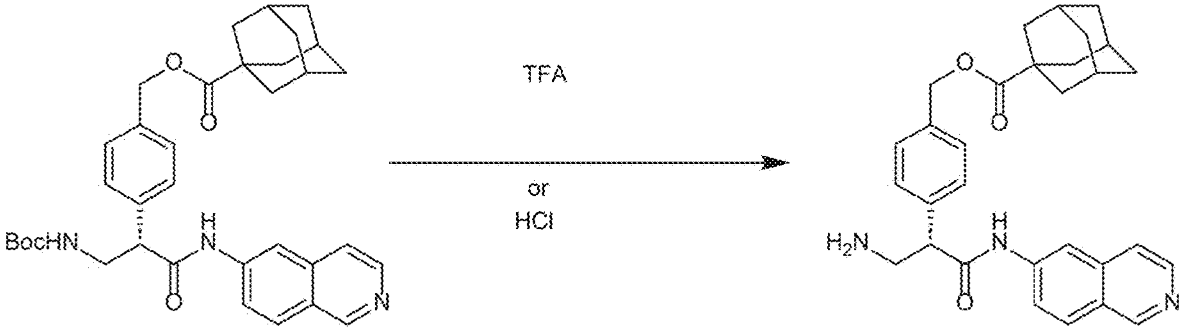
FIG. 4 depicts a synthetic scheme for preparing Compound 1 from Compound C.

In some embodiments, Compound 1 may be prepared from Compound C by deprotection of the Boc protecting group as depicted in FIG. 4; formula (I) or formula (II) may be similarly prepared by deprotection of the Boc protecting group of either formula (III) or formula (IV).

Figure 14:
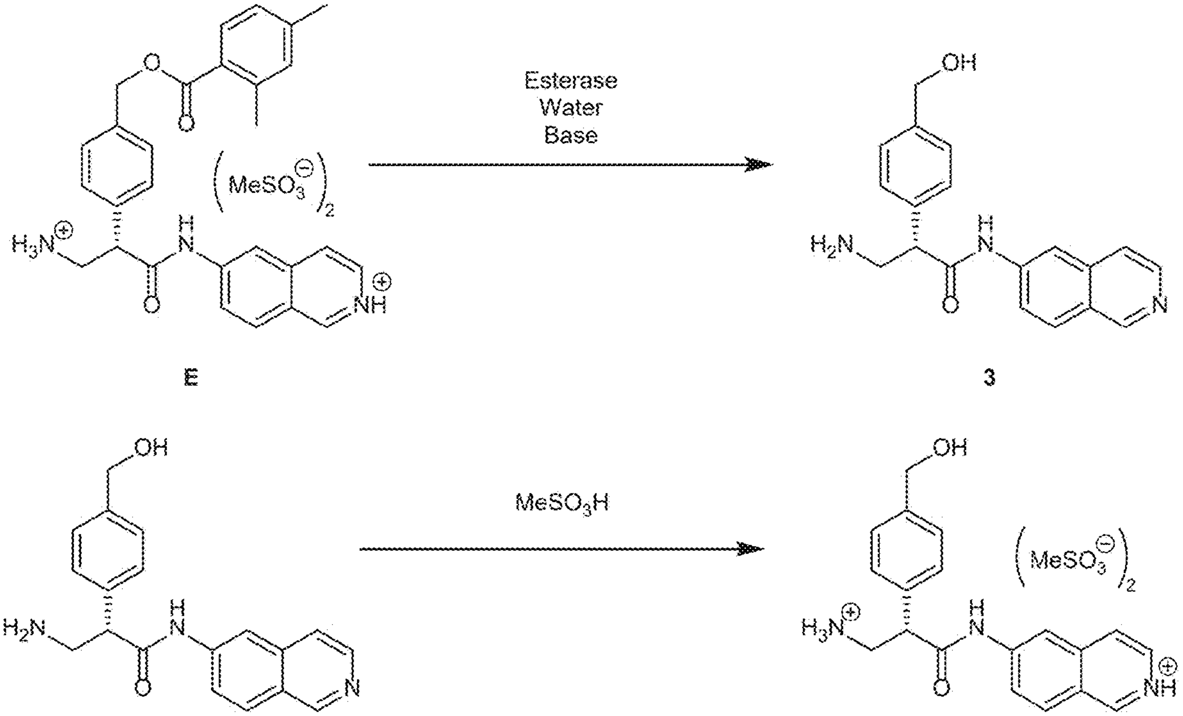
FIG. 14 depicts a synthetic scheme for preparing Compound 4 from Compound E.
Figure 15:
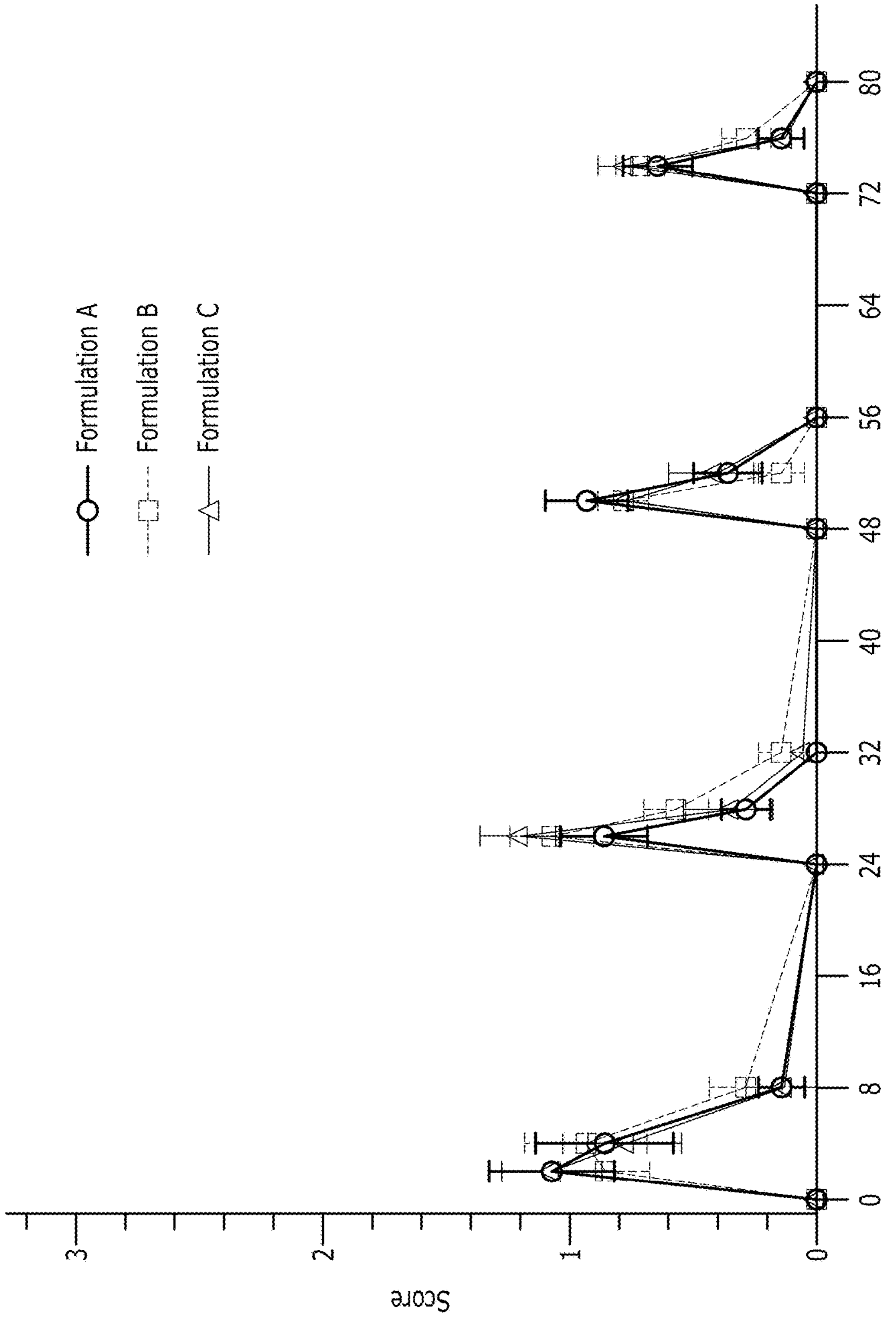
FIG. 15 depicts mean hyperemia scores±standard error of the mean (SEM) of Formulation A, Formulation B, and Formulation C in the study described in Example 16.
Figure 16:
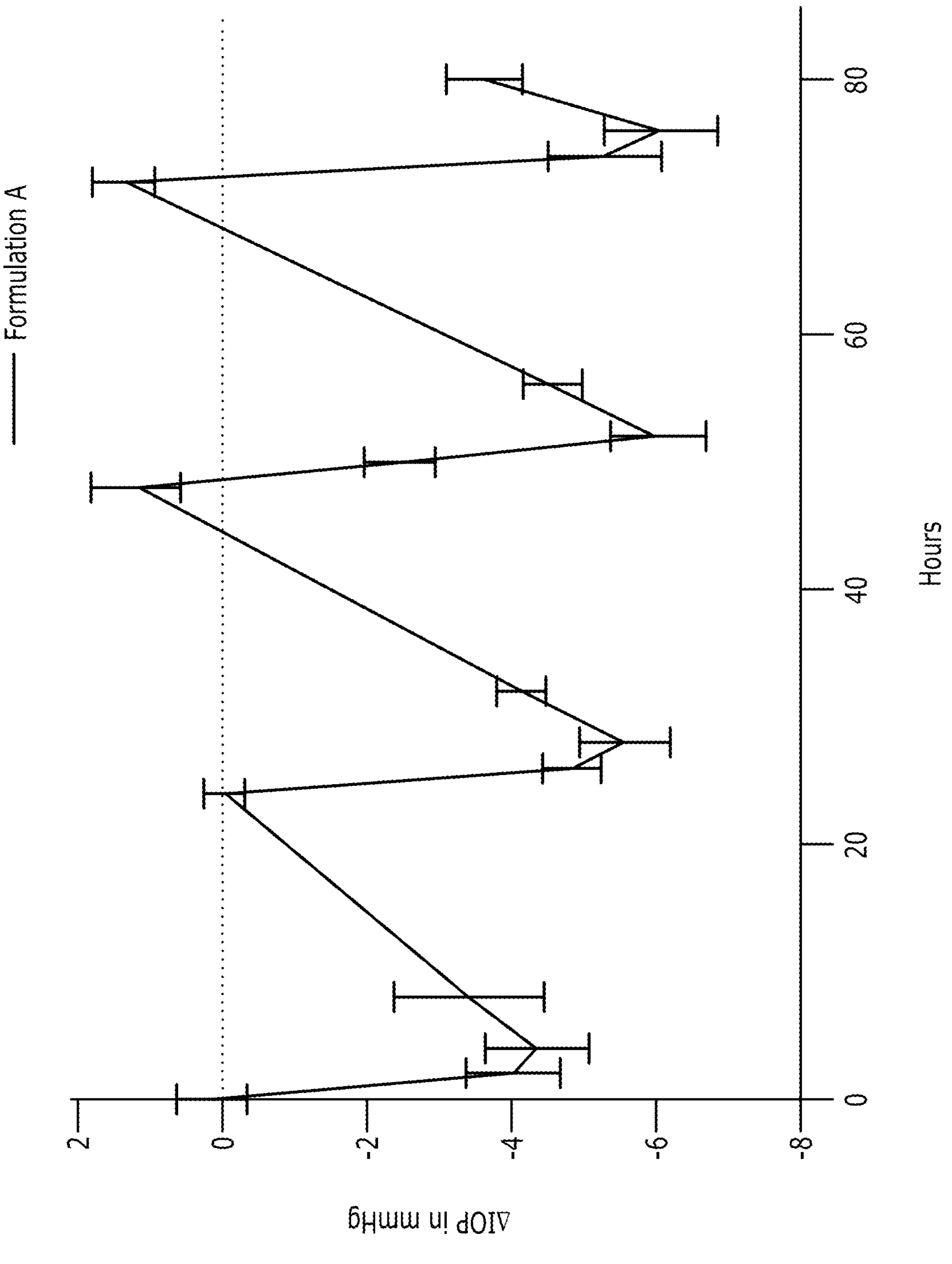
FIG. 16 depicts the difference in mean IOP (OD-OS) between an eye treated with Formulation A (OD) and an untreated eye (OS) according to the study described in Example 16.
Figure 17:
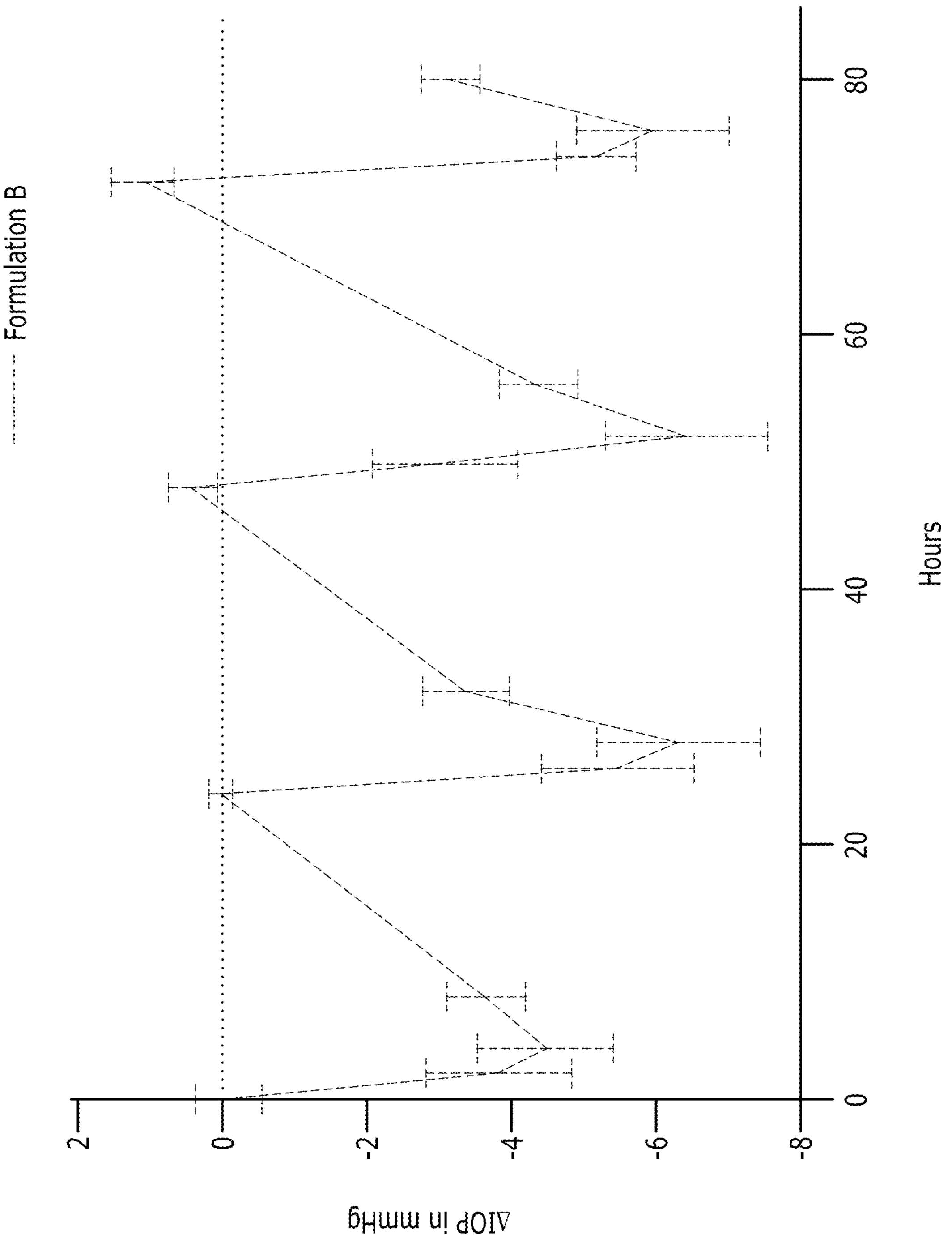
FIG. 17 depicts the difference in mean IOP (OD-OS) between an eye treated with Formulation B (OD) and an untreated eye (OS) according to the study described in Example 16.
Figure 18:
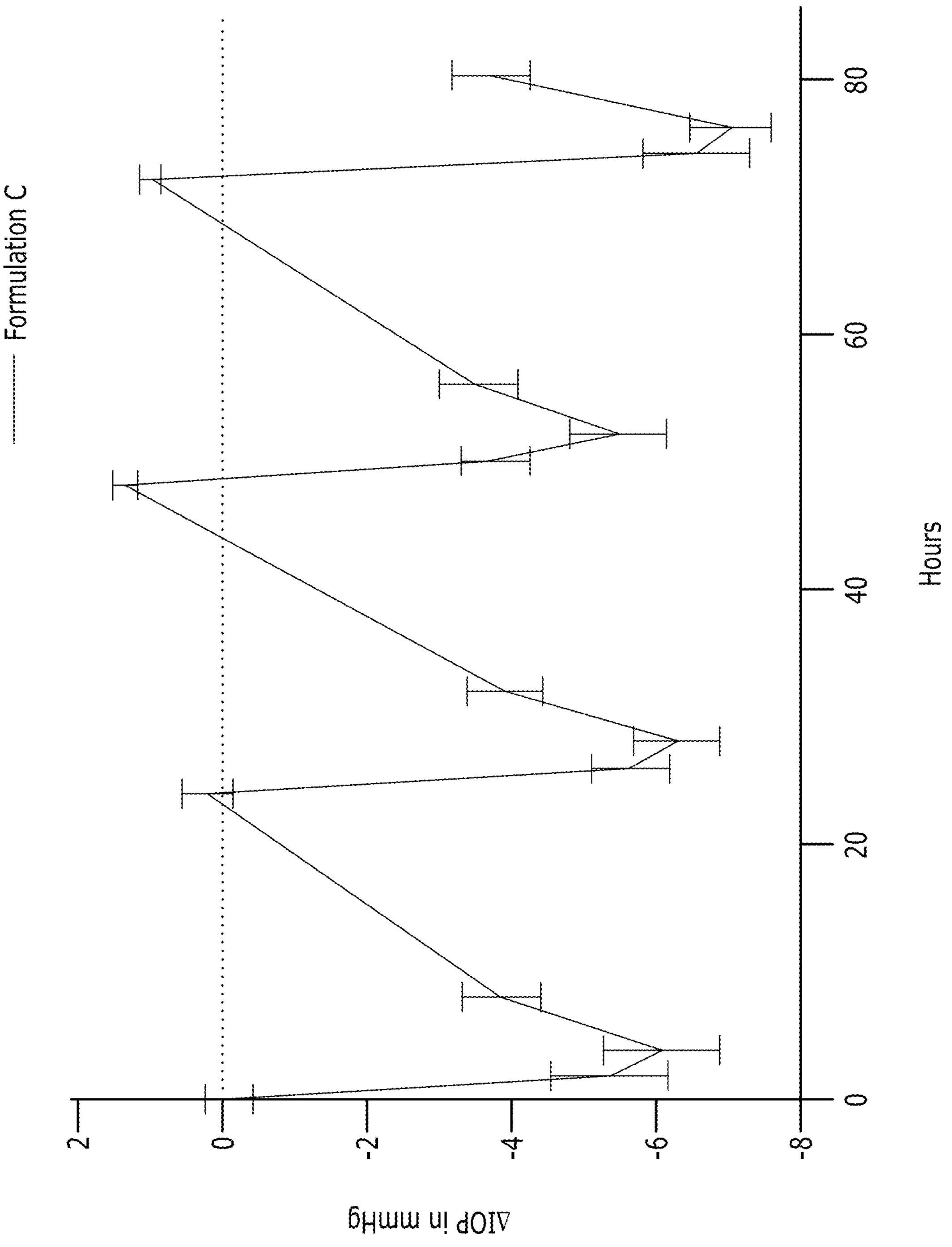
FIG. 18 depicts the difference in mean IOP (OD-OS) between an eye treated with Formulation C (OD) and an untreated eye (OS) according to the study described in Example 16.
Figure 19:
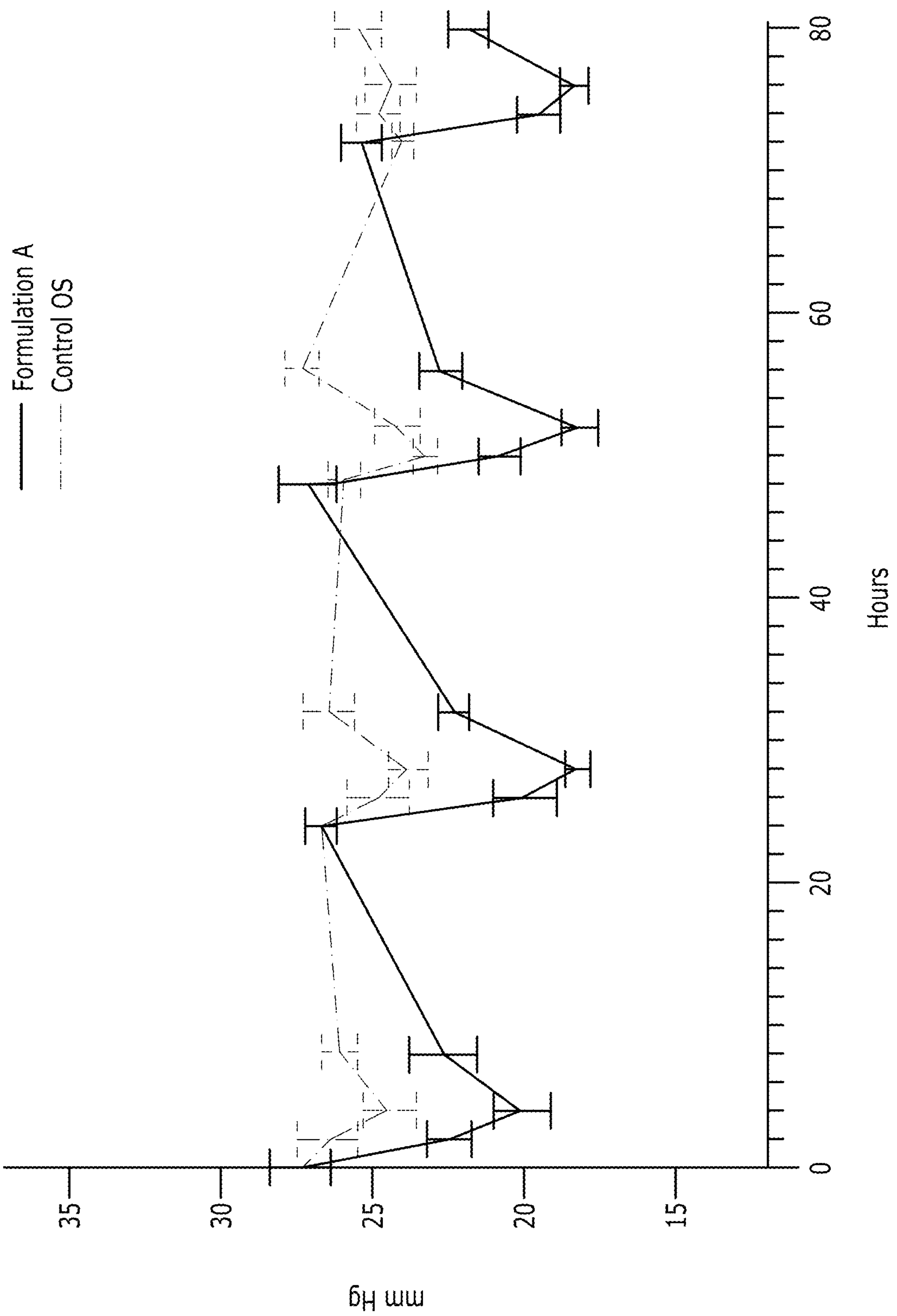
FIG. 19 depicts the mean IOP in an eye treated with Formulation A (OD) and an untreated eye (OS) according to the study described in Example 16.
Figure 20:
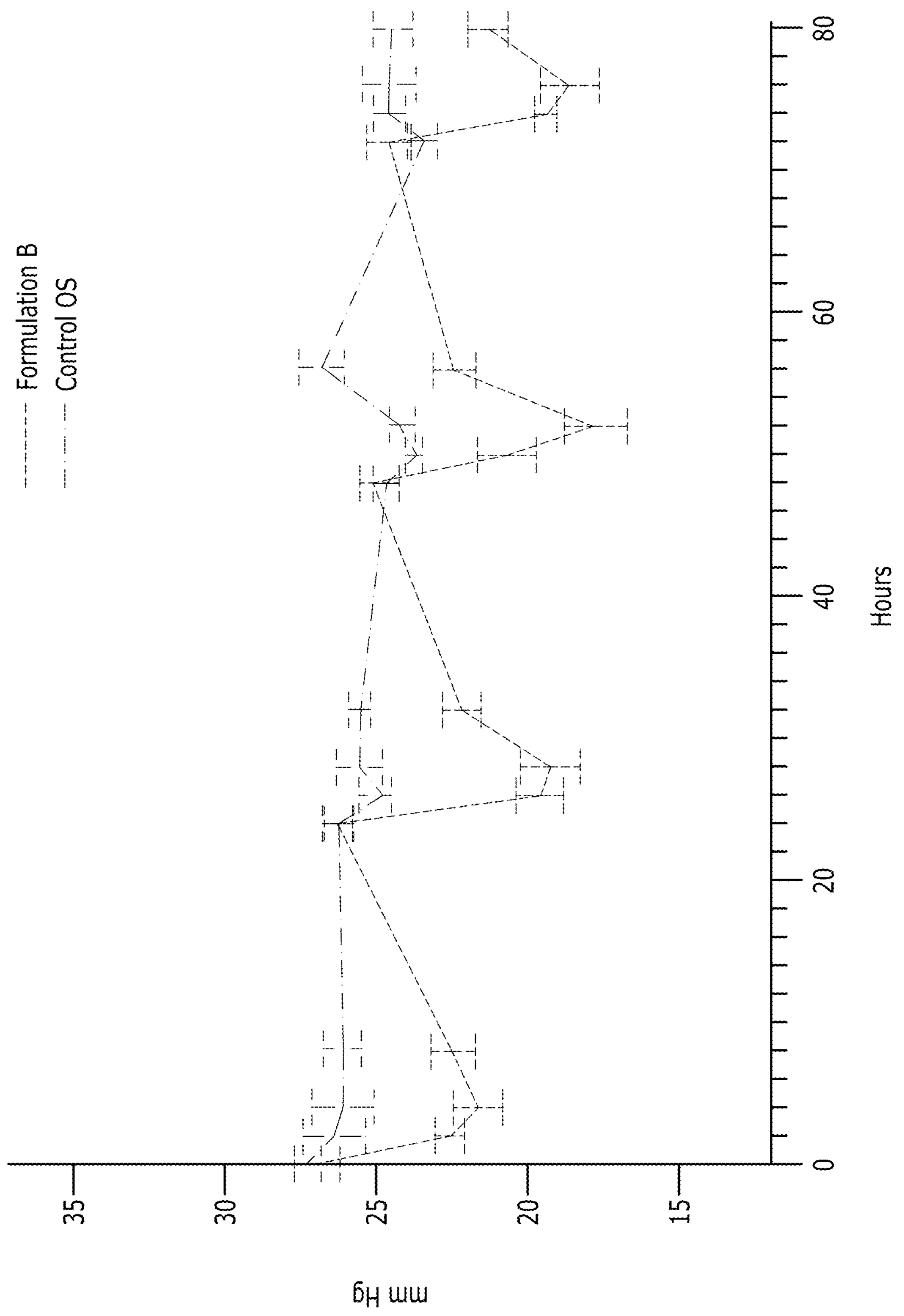
FIG. 20 depicts the mean IOP in an eye treated with Formulation B (OD) and an untreated eye (OS) according to the study described in Example 16.
Figure 21:
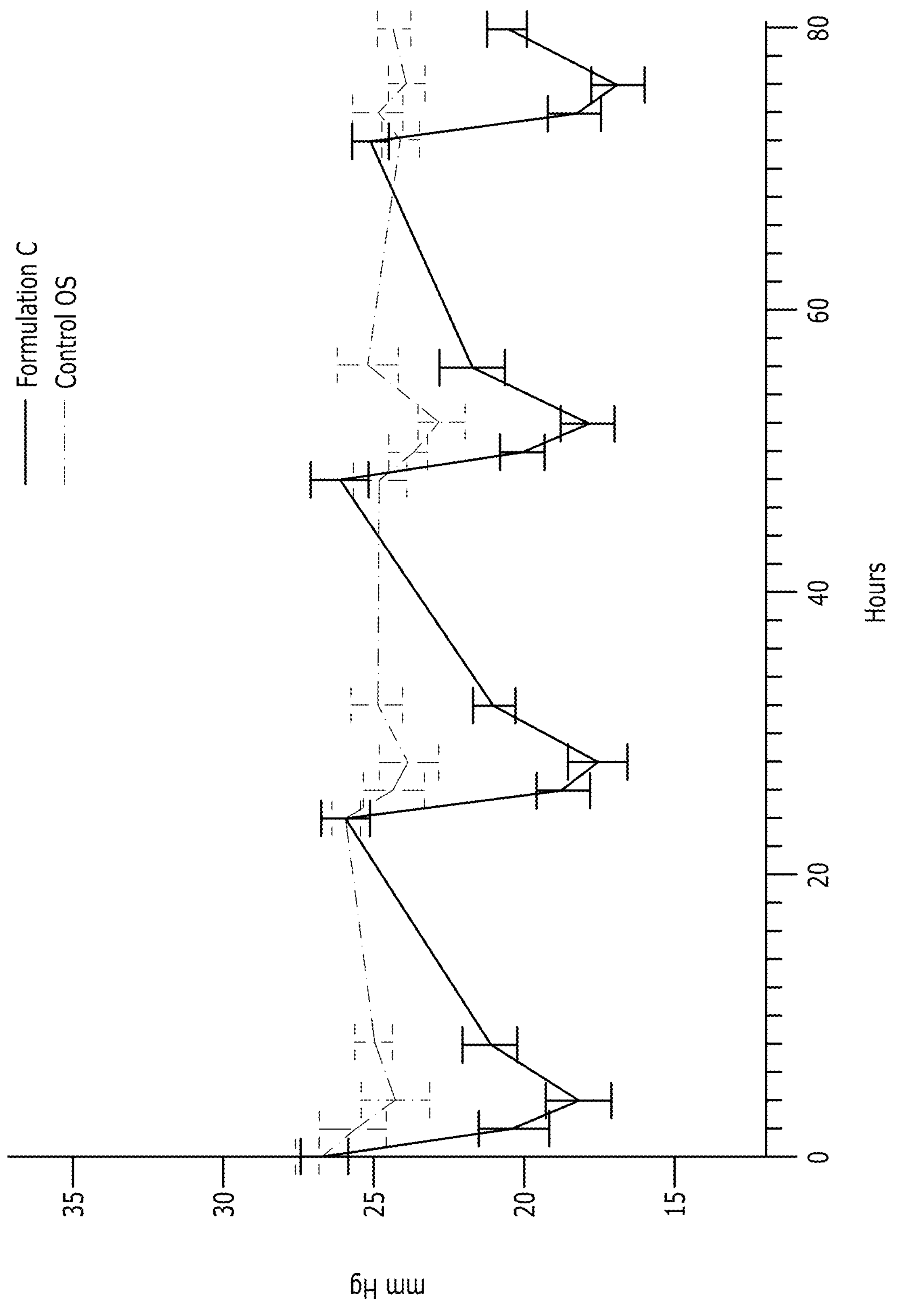
FIG. 21 depicts the mean IOP in an eye treated with Formulation C (OD) and an untreated eye (OS) according to the study described in Example 16.

In some embodiments, Compound 4 may be prepared by treatment of Compound 3 with a solution of $MeSO_3H$ in a solvent (e.g., dichloromethane) as depicted in FIG. 14.

In some embodiments, Compound 3 may be prepared by treatment of Compound E with a solution of an esterase and a base in a solvent (e.g., including water) as depicted in FIG. 14.

Figure 13:
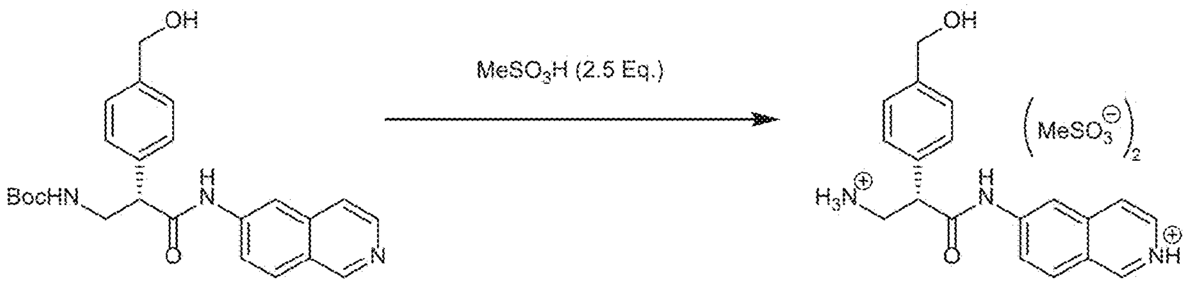
FIG. 13 depicts a synthetic scheme for preparing Compound 4 from Compound B.

In some embodiments, Compound 4 may be prepared by treatment of Compound B with a solution of $MeSO_3H$ in a solvent (e.g., dichloromethane) as depicted in FIG. 13.

The compounds described herein may be isolated and purified by methods well-known to those skilled in the art in the field of organic synthesis, including appropriate substitution of starting materials. Examples of conventional methods for isolating and purifying compounds can include those described, for instance, in "Vogel's Textbook of Practical Organic Chemistry," 5th edition (1989), by Furniss, Hannaford, Smith, and Tatchell, pub. Longman Scientific & Technical, Essex CM20 2JE, England.

Optimum reaction conditions and reaction times for each individual synthetic step can vary depending on the reactants employed and substituents present in the reactants used. Specific procedures are provided in the Examples section below. Reactions can be worked up in the conventional manner, e.g., by eliminating the solvent from the residue and further purified according to methodologies generally known in the art. Unless otherwise described, the starting materials and reagents are either commercially available or can be prepared by one skilled in the art from commercially available materials using methods described in the chemical literature. Suitable protecting groups and the methods for protecting and deprotecting different substituents using such suitable protecting groups are well known to those skilled in the art, examples of which can be found in PGM Wuts and TW Greene, in Greene's book titled Protective Groups in Organic Synthesis (4th ed.), John Wiley & Sons, NY (2006), which is incorporated herein by reference in its entirety. It can be appreciated that the synthetic schemes and specific examples as described are illustrative and are not to be read as limiting the scope of the present disclosure as specified in the appended claims. All alternatives, modifications, and equivalents of the synthetic methods and specific examples are included within the scope of the claims.

Compositions

The compounds herein may be provided in a composition, which may be a pharmaceutical composition comprising a pharmaceutically acceptable carrier. Thus, in some embodiments, provided herein are compositions comprising Compound 1 or a salt thereof or Compound 2 or a salt thereof, and a pharmaceutically acceptable carrier. In some embodiments, the compositions comprise a monomesylate or dimesylate salt of Compound 1. The compositions herein may further include a second therapeutic agent selected from a prostaglandin, optionally in addition to a pharmaceutically acceptable carrier. Thus, in some embodiments, provided herein are compositions comprising a first compound selected from Compound 1 or a salt thereof or Compound 2 or a salt thereof, and a second compound selected from an alpha agonist, a beta blocker, a carbonic anhydrase inhibitor, a cholinergic, a prostaglandin analog, or a rho kinase inhibitor other than the first compound. In some embodiments, provided herein are compositions comprising a first compound selected from Compound 1 or a salt thereof or Compound 2 or a salt thereof, and a second compound selected from bimatoprost, travoprost, latanoprost, or tafluprost. In some embodiments, the second compound is latanoprost. In some embodiments, provided herein are compositions comprising a first compound selected from Compound 1 or a salt thereof, and latanoprost. In some embodiments, provided herein are compositions comprising a compound selected from a dimesylate salt of Compound 1 and latanoprost, and a pharmaceutically acceptable carrier. In some embodiments, provided herein are compositions comprising a compound selected from a dimesylate salt of Compound 1, and a pharmaceutically acceptable carrier. In some embodiments, the compositions herein comprise a salt (e.g., a specific salt form described herein, e.g., a dimesylate salt) of Compound 1, or a salt (e.g., a specific salt form described herein, e.g., a dimesylate salt) of Compound 2, at about 0.01, 0.02, 0.03, 0.04, 0.05, or 0.06% w/v, and optionally include latanoprost at about 0.005% w/v. In some embodiments, provided herein are compositions comprising a compound selected from a monomesylate salt of Compound 1 and latanoprost, and a pharmaceutically acceptable carrier. In some embodiments, provided herein are compositions comprising a compound selected from a monomesylate salt of Compound 1, and a pharmaceutically acceptable carrier. In some embodiments, the compositions herein comprise a salt (e.g., a specific salt form described herein, e.g., a monomesylate salt) of Compound 1, or a salt (e.g., a specific salt form described herein, e.g., a monomesylate salt) of Compound 2, at about 0.01, 0.02, 0.03, 0.04, 0.05, or 0.06% w/v, and optionally include latanoprost at about 0.005% w/v.

Methods

The compounds (e.g., a compound of formula (I) or (II) or a pharmaceutically acceptable salt thereof) and compositions herein are useful ROCK inhibitors, and accordingly may be used to treat diseases associated with ROCK inhibition, e.g., diseases including asthma, cancer, cardiovascular disease, erectile dysfunction, glaucoma, insulin resistance, kidney failure, neuronal degeneration (e.g., cerebral vasospasm), and osteoporosis. The compounds and compositions herein are useful in treating glaucoma (e.g., primary open-angle glaucoma or angle-closure glaucoma).

The compounds (e.g., a compound of formula (I) or (II) or a pharmaceutically acceptable salt thereof) and compositions herein may, in some embodiments, be administered via a variety of routes, including ocular instillation. Accordingly, provided herein are methods of administration, comprising ocular instillation of a compound or composition described herein.

The compounds (e.g., a compound of formula (I) or (II) or a pharmaceutically acceptable salt thereof) and compositions herein are useful in reducing intraocular pressure, and thereby are useful in treating ocular hypertension or glaucoma, e.g., primary open-angle glaucoma or angle-closure glaucoma.

Thus, in some embodiments, provided herein are methods of treating glaucoma (e.g., primary open-angle glaucoma) in a subject in need thereof, comprising administration of a compound (e.g., a compound of formula (I) or (II) or a pharmaceutically acceptable salt thereof) or composition herein to the subject. In some embodiments, provided herein are methods of treating glaucoma (e.g., primary open-angle glaucoma or angle-closure glaucoma), comprising administration of Compound 1 or a salt thereof (e.g., a monomesylate or dimesylate salt) or Compound 2 or a salt thereof (e.g., a monomesylate or dimesylate salt) to a subject in need thereof. In some embodiments, the administration can include administration of a composition comprising Compound 1 or a salt thereof or Compound 2 or a salt thereof. In some embodiments, the administered composition is a pharmaceutical composition further comprising a pharmaceutically acceptable carrier. In some embodiments, the administration further comprises administration of a second compound selected from an alpha agonist, a beta blocker, a carbonic anhydrase inhibitor, a cholinergic, a prostaglandin analog, or a rho kinase inhibitor other than Compound 1 or Compound 2 or their salts. In some embodiments, the administration further comprises administration of a second compound selected from an alpha agonist, a beta blocker, a carbonic anhydrase inhibitor, a cholinergic, a prostaglandin analog, or a rho kinase inhibitor other than Compound 1 or Compound 2 or their salts, and a pharmaceutically acceptable carrier.

Thus, in some embodiments, provided herein are methods of treating glaucoma (e.g., primary open-angle glaucoma or angle-closure glaucoma) in a subject in need thereof, comprising administration of Compound 1 or a salt thereof or Compound 2 or a salt thereof to the subject. In other embodiments, provided herein are methods of treating glaucoma (e.g., primary open-angle glaucoma or angle-closure glaucoma) in a subject in need thereof, comprising administration of a composition to the subject, the composition comprising Compound 1 or a salt thereof (e.g., a monomesylate or dimesylate salt) or Compound 2 or a salt thereof (e.g., a monomesylate or dimesylate salt), and a pharmaceutically acceptable carrier.

Thus, in some embodiments, provided herein are methods of treating glaucoma (e.g., primary open-angle glaucoma or angle-closure glaucoma) in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof (e.g., a monomesylate or dimesylate salt) or Compound 2 or a salt thereof (e.g., a monomesylate or dimesylate salt), and a second compound selected from an alpha agonist, a beta blocker, a carbonic anhydrase inhibitor, a cholinergic, a prostaglandin analog, or a rho kinase inhibitor other than the first compound. The methods herein may further include administration of a second therapeutic agent selected from an alpha agonist, a beta blocker, a carbonic anhydrase inhibitor, a cholinergic, a prostaglandin analog, or a rho kinase inhibitor other than the first compound. In some embodiments of these methods, the second therapeutic agent is selected from a prostaglandin.

In some embodiments, provided herein are methods of treating glaucoma (e.g., primary open-angle glaucoma or angle-closure glaucoma) in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof (e.g., a monomesylate or dimesylate salt) or Compound 2 or a salt thereof (e.g., a monomesylate or dimesylate salt), and a second compound selected from bimatoprost, travoprost, latanoprost, or tafluprost. In some embodiments, the second compound is latanoprost. In some embodiments, the composition further comprises a pharmaceutically acceptable carrier.

In some embodiments, provided herein are methods of treating glaucoma (e.g., primary open-angle glaucoma or angle-closure glaucoma) in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof, and latanoprost.

In some embodiments, provided herein are methods of treating glaucoma (e.g., primary open-angle glaucoma or angle-closure glaucoma) in a subject in need thereof, comprising administration of a composition to the subject, the composition comprising a compound (e.g., a compound of formula (I) or (II) or a pharmaceutically acceptable salt thereof), which may be selected from a monomesylate or dimesylate salt of Compound 1 and latanoprost, and a pharmaceutically acceptable carrier.

In some embodiments, provided herein are methods of treating glaucoma (e.g., primary open-angle glaucoma or angle-closure glaucoma) in a subject in need thereof, comprising administration of a composition to the subject, the composition comprising a compound (e.g., a compound of formula (I) or (II) or a pharmaceutically acceptable salt thereof), which may be selected from a monomesylate or dimesylate salt of Compound 1, and a pharmaceutically acceptable carrier.

In other embodiments, provided herein are methods of treating ocular hypertension in a subject in need thereof, comprising administration of a compound herein (e.g., a compound of formula (I) or (II) or a pharmaceutically acceptable salt thereof), which may be Compound 1 or a salt thereof (e.g., a monomesylate or dimesylate salt) or Compound 2 or a salt thereof (e.g., a monomesylate or dimesylate salt) to the subject. In some embodiments, provided herein are methods of treating ocular hypertension in a subject in need thereof, comprising administration of a composition to the subject, the composition comprising Compound 1 or a salt thereof (e.g., a monomesylate or dimesylate salt) or Compound 2 or a salt thereof (e.g., a monomesylate or dimesylate salt), and a pharmaceutically acceptable carrier.

Thus, in some embodiments, provided herein are methods of treating ocular hypertension in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof or Compound 2 or a salt thereof, and a second compound selected from an alpha agonist, a beta blocker, a carbonic anhydrase inhibitor, a cholinergic, a prostaglandin analog, or a rho kinase inhibitor other than the first compound. The methods herein may further include administration of a second therapeutic agent selected from an alpha agonist, a beta blocker, a carbonic anhydrase inhibitor, a cholinergic, a prostaglandin analog, or a rho kinase inhibitor other than the first compound. In some embodiments of these methods, the second therapeutic agent is selected from a prostaglandin.

In some embodiments, provided herein are methods of treating ocular hypertension in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof or Compound 2 or a salt thereof, and a second compound selected from bimatoprost, travoprost, latanoprost, or tafluprost. In some embodiments, the second compound is latanoprost.

In some embodiments, provided herein are methods of treating ocular hypertension in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof, and latanoprost.

In some embodiments, provided herein are methods of treating ocular hypertension in a subject in need thereof, comprising administration of a composition to the subject, the composition comprising a compound (e.g., a compound of formula (I) or (II) or a pharmaceutically acceptable salt thereof), which may be selected from a monomesylate or dimesylate salt of Compound 1 and latanoprost, and a pharmaceutically acceptable carrier.

In some embodiments, provided herein are methods of treating ocular hypertension in a subject in need thereof, comprising administration of a composition to the subject, the composition comprising a compound (e.g., a compound of formula (I) or (II) or a pharmaceutically acceptable salt thereof), which may be selected from a monomesylate or dimesylate salt of Compound 1, and a pharmaceutically acceptable carrier.

The compounds and compositions herein are also useful in treating eye diseases, including, but not limited to, corneal endothelial dystrophy, ocular fibrotic diseases and disorders, and retinal diseases such as wet AMD, dry AMD, and diabetic retinopathy, as well as Fuchs corneal endothelial dystrophy.

Thus, in still other embodiments, provided herein are methods of treating an eye disease, including, but not limited to, corneal endothelial dystrophy, ocular fibrotic diseases and disorders, and retinal diseases such as wet AMD, dry AMD, and diabetic retinopathy, as well as Fuchs corneal endothelial dystrophy, in a subject in need thereof, comprising administration of a compound (e.g., a compound of formula (I) or (II) or a pharmaceutically acceptable salt thereof) or composition herein to the subject. In some embodiments, provided herein are methods of treating an eye disease, including, but not limited to, corneal endothelial dystrophy, ocular fibrotic diseases and disorders, and retinal diseases such as wet AMD, dry AMD, and diabetic retinopathy, as well as Fuchs corneal endothelial dystrophy, in a subject in need thereof, comprising administration of Compound 1 or a salt thereof (e.g., a monomesylate or dimesylate salt) or Compound 2 or a salt thereof (e.g., a monomesylate or dimesylate salt) to the subject. In some embodiments, the administration can include administration of a composition comprising Compound 1 or a salt thereof or Compound 2 or a salt thereof. In some embodiments, the administered composition is a pharmaceutical composition further comprising a pharmaceutically acceptable carrier. In some embodiments, the administration further comprises administration of a second compound selected from an alpha agonist, a beta blocker, a carbonic anhydrase inhibitor, a cholinergic, a prostaglandin analog, or a rho kinase inhibitor other than Compound 1 or Compound 2 or their salts. In some embodiments of these methods, the second therapeutic agent or compound is selected from a prostaglandin, e.g., latanoprost.

In other embodiments, provided herein are methods of inhibiting a ROCK (e.g., ROCK1 or ROCK 2, or both ROCK1 and ROCK2), comprising contacting the ROCK with a compound herein (e.g., a compound of formula (I) or (II) or a pharmaceutically acceptable salt thereof), which may be Compound 1 or a salt thereof or Compound 2 or a salt thereof. In some embodiments of these methods, the ROCK inhibition is in vitro. In some embodiments of these methods, the ROCK inhibition is in vivo. In some embodiments, provided herein are methods of inhibiting ROCK (e.g., ROCK1 or ROCK 2, or both ROCK1 and ROCK2) in a subject in need thereof, comprising administration of a composition, the composition comprising Compound 1 or a salt thereof or Compound 2 or a salt thereof, and a pharmaceutically acceptable carrier.

Thus, in some embodiments, provided herein are methods of inhibiting ROCK (e.g., ROCK1 or ROCK 2, or both ROCK1 and ROCK2) in a subject in need thereof, comprising administration of a composition to the subject, the composition comprising a first compound selected from Compound 1 or a salt thereof (e.g., a monomesylate or dimesylate salt) or Compound 2 or a salt thereof (e.g., a monomesylate or dimesylate salt), and a second compound selected from an alpha agonist, a beta blocker, a carbonic anhydrase inhibitor, a cholinergic, a prostaglandin analog, or a rho kinase inhibitor other than the first compound. The methods herein may further include administration of a second therapeutic agent selected from an alpha agonist, a beta blocker, a carbonic anhydrase inhibitor, a cholinergic, a prostaglandin analog, or a rho kinase inhibitor other than the first compound. In some embodiments of these methods, the second therapeutic agent is selected from a prostaglandin.

In some embodiments, provided herein are methods of inhibiting ROCK (e.g., ROCK1 or ROCK 2, or both ROCK1 and ROCK2) in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof or Compound 2 or a salt thereof, and a second compound selected from bimatoprost, travoprost, latanoprost, or tafluprost. In some embodiments, the second compound is latanoprost.

In some embodiments, provided herein are methods of inhibiting ROCK (e.g., ROCK1 or ROCK 2, or both ROCK1 and ROCK2) in a subject in need thereof, comprising administration of a composition to the subject, the composition comprising a first compound (e.g., a compound of formula (I) or (II) or a pharmaceutically acceptable salt thereof), which may be selected from Compound 1 or a salt thereof (e.g., a monomesylate or dimesylate salt), and latanoprost.

In some embodiments, provided herein are methods of inhibiting ROCK (e.g., ROCK1 or ROCK 2, or both ROCK1 and ROCK2) in a subject in need thereof, comprising administration of a composition to the subject, the composition comprising a monomesylate or dimesylate salt of Compound 1 and latanoprost, and a pharmaceutically acceptable carrier.

In some embodiments, provided herein are methods of inhibiting ROCK (e.g., ROCK1 or ROCK 2, or both ROCK1 and ROCK2) in a subject in need thereof, comprising administration of a composition to the subject, the composition comprising a monomesylate or dimesylate salt of Compound 1, and a pharmaceutically acceptable carrier.

In some embodiments of the methods herein, the subject is a mammal, such as a human subject.

In some embodiments of the methods herein, the first compound (e.g., a compound of formula (I) or (II) or a pharmaceutically acceptable salt thereof) and the second compound are administered as a fixed dose combination (i.e. in an admixture composition). In some embodiments, the composition herein comprises the first compound at about 0.01, 0.02, 0.03, or 0.04% w/v (calculated according to the free base of the first compound including when the first compound is provided as a salt form), and optionally includes the second compound at about 0.001 to about 0.005% w/v. In some embodiments, the first compound (e.g., the adamantanyl compound such as the monomesylate or dimesylate of Compound 1) is administered as a fixed dose combination with latanoprost. In some embodiments, the first compound is a monomesylate or dimesylate salt of Compound 1 and the second compound is latanoprost. In some embodiments, the composition herein comprises a monomesylate or dimesylate salt of Compound 1 or a monomesylate or dimesylate salt of Compound 2 at about 0.01, 0.02, 0.03, or 0.04% w/v (calculated according to the free base of the compound in salt form), and optionally includes latanoprost at about 0.005% w/v.

In some embodiments, provided herein are methods of inhibiting ROCK (e.g., ROCK1 or ROCK 2, or both ROCK1 and ROCK2) in a subject in need thereof, comprising administration of a composition, the composition comprising a monomesylate or dimesylate salt of Compound 1 or a monomesylate or dimesylate salt of Compound 2 at about 0.01, 0.02, 0.03, or 0.04% w/v (calculated according to the free base of the compound in salt form), and optionally including latanoprost at about 0.005% w/v.

In some embodiments, provided herein are methods of treating glaucoma in a subject in need thereof, comprising administration of a composition, the composition comprising a monomesylate or dimesylate salt of Compound 1 or a monomesylate or dimesylate salt of Compound 2 at about 0.01, 0.02, 0.03, or 0.04% w/v (calculated according to the free base of the compound in salt form), and optionally including latanoprost at about 0.005% w/v.

In some embodiments, provided herein are methods of treating ocular hypertension in a subject in need thereof, comprising administration of a composition, the composition comprising a monomesylate or dimesylate salt of Compound 1 or a monomesylate or dimesylate salt of Compound 2 at about 0.01, 0.02, 0.03, or 0.04% w/v (calculated according to the free base of the compound in salt form), and optionally including latanoprost at about 0.005% w/v.

In some embodiments, provided herein are methods of reducing intraocular pressure in a subject in need thereof, comprising administration of a composition, the composition comprising a monomesylate or dimesylate salt of Compound 1 or a monomesylate or dimesylate salt of Compound 2 at about 0.01, 0.02, 0.03, or 0.04% w/v (calculated according to the free base of the compound in salt form), and optionally including latanoprost at about 0.005% w/V.

In some embodiments of the methods herein, the compound is an adamantanyl compound herein or a pharmaceutically acceptable salt thereof. In some embodiments of the methods herein, the compound is a monomesylate or dimesylate salt of Compound 1 (e.g., Compound D).

In some embodiments of these methods, the administration is to a plurality of subjects, wherein the administration results in the subjects experiencing statistically significant (95% confidence interval (CI)) on average less hyperemia as compared to analogous administration of netarsudil.

In some embodiments of these methods, the administration is to a plurality of subjects, wherein the administration results in the subjects experiencing statistically significant (95% CI) on average improved reduction of intraocular pressure as compared to analogous administration of netarsudil.

Kits

In some embodiments, provided herein are packaged dosage forms, comprising a container holding a therapeutically effective amount of Compound 1 or a salt thereof or Compound 2 or a salt thereof, and instructions for using the dosage form in accordance with one or more of the methods provided herein.

Such dosage forms and associated materials can be finished as a commercial product by the usual steps performed in the present field, for example by appropriate sterilization and packaging steps. For example, the material can be treated by UV/vis irradiation (200-500 nm), for example using photo-initiators with different absorption wavelengths (for example, Irgacure 184, 2959), preferably water-soluble initiators (for example, Irgacure 2959). Such irradiation is usually performed for an irradiation time of 1-60 min, but longer irradiation times may be applied, depending on the specific method. The material according to the present disclosure can be finally sterile-wrapped so as to retain sterility until use and packaged (for example, by the addition of specific product information leaflets) into suitable containers (boxes, etc.).

According to further embodiments, the described dosage forms can also be provided in kit form combined with other components necessary for administration of the material to the patient. For example, disclosed kits, such as for use in the treatments described herein, can further comprise, for example, administration materials.

The kits may be designed in various forms based on the specific deficiencies they are designed to treat.

When the dosage forms provided herein are stored in a polyolefin plastic container as compared to, for example, a polyvinyl chloride plastic container, discoloration of the dosage form may be reduced. Without being bound by theory, the container may reduce exposure of the container's contents to electromagnetic radiation, whether visible light (for example, having a wavelength of about 380-780 nm) or ultraviolet (UV) light (for example, having a wavelength of about 190-320 nm (UV B light) or about 320-380 nm (UV A light)). Some containers also include the capacity to reduce adherence or adsorption of the active ingredient to the surface of the container, which could effectively dilute the concentration of active ingredient in the contained solution. Some containers also include the capacity to reduce exposure of the container's contents to infrared light, or a second component with such a capacity. Some containers further include the capacity to reduce the exposure of the container's contents to heat or humidity. The containers that may be used include those made from a polyolefin such as polyethylene, polypropylene, polyethylene terephthalate, polycarbonate, polymethylpentene, polybutene, or a combination thereof, especially polyethylene, polypropylene, or a combination thereof. In some embodiments, the container is a glass container. The container may further be disposed within a second container, for example, a paper container, cardboard container, paperboard container, metallic film container, or foil container, or a combination thereof, to further reduce exposure of the container's contents to UV, visible, or infrared light. Articles of manufacture benefiting from reduced discoloration, decomposition, or both during storage, include dosage forms that include Compound 1 or a salt thereof or Compound 2 or a salt thereof. The dosage forms provided herein may need storage lasting up to, or longer than, three months; in some cases, up to, or longer than one year. The containers may be in any form suitable to contain the contents—for example, a bag, a bottle, or a box.

EXAMPLES

The following examples further illustrate embodiments of the present disclosure. However, they are in no way a limitation of the teachings or disclosure as described herein. Unless otherwise stated, the examples were conducted at standard temperature (e.g. about 20-25° C.) and standard pressure (e.g., atmospheric pressure) and under conditions otherwise commonly applying to these kinds of examples.

Example 1: Synthesis of Compound B (tert-butyl (S)-(2-(4-(hydroxymethyl)phenyl)-3-(isoquinolin-6-ylamino)-3-oxopropyl) carbamate)

FIG. 1 depicts a synthetic scheme for preparing Compound B.

(S)-tert-butyl 2-(4-(hydroxymethyl)phenyl)-3-(isoquinolin-ylamino)-3-oxopropylcarbamate (Compound B). To Compound A (250 g, 0.452 mol) in DMSO (2411 mL) was added HPG Cyclodextrin (500 g) with additional DMSO (97 mL) and the mixture was dissolved at 40° C. To a separate reaction vessel was added HPG Cyclodextrin (500 g in KH2PO4 buffer (0.1 M, 2000 mL)), Codexis Esterase (20% w/v, 50 g, in KH2PO4 (0.1M, 2000 mL, pH 7.3)) and additional KH2PO4 (0.1 M, 3500 mL, pH 7.3). The esterase/cyclodextrin/buffer solution was warmed to 30±5° C. while stirring. The Compound A/cyclodextrin/DMSO solution was slowly added to the buffer/esterase reaction vessel via addition funnel and the flask and funnel were rinsed with DMSO (706 mL) and added to the buffer reaction. The reaction was stirred at 30±5° C.

After 46 hours, the reaction was diluted with purified water (7500 mL) and sodium chloride (2500 g) and 2-methyl THF (18.9 L) were added and stirred at 30±5° C. for 1 hour. The layers were settled and separated the organic layer was further extracted with 2-Me-THF (2×18.9 L). The organic extracts were filtered through a Meissner 5 um Vanguard filtration cartridge followed by subsequent filtration through a Florisil bed (625 g) rinsing with additional 2-MeTHF (3×7.5 L). The filtered organic extracts were transferred to a clean 100 L reaction vessel and washed with $KHCO_3$ (aqueous, 10% 2×7.5 L) and K2CO3 (aqueous, 2.5%, 2×7.5 L) and sodium chloride (aqueous, 14%, 7.5 L). The organic extracts were dried Na2SO4 (2500 g), filtered. The organic extracts were concentrated to give crude Compound B. Column chromatography of crude Compound B using a Biotage 5 kg HP-Sphere cartridge equilibrated with dichloromethane was used. Compound B was dissolved in dichloromethane/methanol, absorbed onto Florisil then transferred to a SIM in which the eluent was passed through. The column was eluted with 3% methanol in dichloromethane to remove the unreacted Compound A followed by 5% methanol in dichloromethane then 7% methanol in dichloromethane to collect(S)-tert-butyl 2-(4-(hydroxymethyl)phenyl)-3-(isoquinolin-6-ylamino)-3-oxopropylcarbamate (Compound B, 171.4 g, 90%)

Alternate Route to Compound B through LAH Reduction of Compound A.

Compound A (7.5 g, 13.6 mmol, 1.0 eq) was dissolved in THF (75 mL, 10 volumes) at 35° C. then cooled to −15° C. LAH (1.0 M in THF, 27.1 mL, 27.1 mmol, 2 eq) was added over 60 min. After 3 hours Rochelle's salt (25% aqueous, 15 mL) was added while keeping the temperature to below 5° C. The reaction mixture was filtered and the organic layer was washed with water (3×5 volumes), evaporated and chased with acetonitrile to give crude Compound B. To Crude Compound B was added acetonitrile (10 Vol) and heated to dissolve (79° C.). The solution was slowly cooled to 20° C. over 12 h and held overnight. The recrystallized solids were filtered and washed with acetonitrile at −15° C. to give 3.85 g, 67% yield of pure Compound B.

Example 2: Synthesis of Compound C (4-((S)-3-((tert-butoxycarbonyl)amino)-1-(isoquinolin-6-ylamino)-1-oxopropan-2-yl)benzyl adamantane-1-carboxylate)

FIG. 1 and FIG. 2 depict synthetic schemes for preparing Compound C.

Compound B (162.9 g, 0.386 mol), 1-ADCA (73.2 g, 0.41 mol), EDC·HCl (96.4 g, 0.50 mol), and DMAP (47.3 g, 0.39 mol) were charged to a clean 10 L jacketed reaction vessel followed by dichloromethane (1629 mL, 10 volumes). The reaction mixture was stirred at 20±5° C. for 18 hours and checked for completion by TLC. The mixture was transferred to a clean 30 L reaction vessel. 2-MeTHF (4073 mL, 25 volumes) was added. The reaction mixture was quenched and washed with 5% aqueous citric acid (2×10 volumes). The aqueous layers from the 5% aqueous citric acid washes were combined then back-extracted with 2-MeTHF (10 volumes). The organic layers were combined and washed with 10% aqueous potassium bicarbonate ($KHCO_3$) (10 volumes), 5% aqueous potassium carbonate ($K_2CO_3$) (10 volumes), then 14% aqueous sodium chloride (NaCl) (10 volumes). The resulting organic layer was dried with sodium sulfate 5 parts), stirred for 48 minutes in the 30 L reactor before filtering the solids on a coarse glass fritted funnel. The filtrate was concentrated on the rotovap. After drying the resulting residue under high vacuum overnight, 247.3 g of Compound C was obtained. The Crude Compound C was purified by column chromatography using a 5 kg 150 L Biotage KP-Sil cartridge, equilibrated with (60:40) heptane/ethyl acetate. The cartridge was eluted with (60:40) heptane/ethyl acetate followed by (30:70) heptane/ethyl acetate and pure fractions were isolated. The resulting residue was chased with of (50:50) dichloromethane/heptane (20 volumes) followed by dichloromethane (20 volumes), then dried under high vacuum to afford 220.3 g of Compound C (97.6%).

The corresponding 2-adamantanyl compound is similarly prepared using adamantane-2-carboxylic acid instead of adamantane-1-carboxylic acid. Similarly, other 1- or 2-adamantanyl compounds are likewise prepared using commercially available adamantane carboxylic acids (e.g., adamantane carboxylic acid substituted with one or more substituents selected, independently from halogen, methyl, ethyl, propyl, or isopropyl) instead of adamantane-1-carboxylic acid, e.g., 3-fluoroadamantane-1-carboxylic acid, 5-bromo-3-methyl-adamantane-1-carboxylic acid, or 3-(1,1,2,3,3,3-hexafluoro-propyl)-adamantane-1-carboxylic acid.

Example 3: Synthesis of Compound D (dimesylate salt of 4-((S)-3-amino-1-(isoquinolin-6-ylamino)-1-oxopropan-2-yl)benzyl adamantane-1-carboxylate)

FIG. 1 depicts a synthetic scheme for preparing Compound D.

Compound C (219.7 g, 0.376 mol) was dissolved in dichloromethane (2196 mL, 10 volumes) and charged to a clean, nitrogen flushed, 10 L jacketed reaction vessel. Methanesulfonic acid (90.4 g, 0.941 mol) in dichloromethane (550 mL, 2.5 volumes) was added to the vessel and additional dichloromethane (550 mL, 2.5 vol) was used to rinse and added to the vessel. The reaction was stirred at 20±5° C. for 20 hours. Then, the reaction mixture was evacuated from the 10 L reaction vessel, rinsing the reactor with isobutanol (1100 mL, 5.0 volumes) and concentrated on the rotovap to afford 299.0 g of Compound D.

The Crude Compound D was dissolved in isobutanol (25 volumes) at 50-55° C. and charged to a clean, pre-rinsed 30 L jacketed reaction vessel. MTBE (440 mL, 2 volumes) was added to the crude Compound D solution at 50±5° C. in the 30 L reaction vessel. Once a homogenized mixture was observed, the content of the 30 L reaction vessel was cooled to 20±5° C. The mixture was further cooled to −20±5° C. MTBE (16.5 L, 75 volumes) was added and the resulting mixture was stirred at −20±5° C. for approximately 30 minutes. The Compound D solid that had precipitated was then filtered under vacuum and a backfill of nitrogen in a 5 L filter reactor fitted with a PTFE membrane filter having a 30-μm porosity. The 30 L reaction vessel was rinsed with MTBE (3×20 volumes) and the solids were dried on the filter under vacuum with a backfill of nitrogen for approximately 35 minutes, then transferred to a tared drying dish. The solid was then dried in a vacuum oven pre-heated to 35±5° C. for 18-24 hours, then at 80±5° C. for an additional 139 hours 6 minutes to give Compound D 242.8 g (90.8% yield across two steps).

The corresponding 2-adamantanyl compound is similarly prepared. Similarly, other 1- or 2-adamantanyl compounds of formulae (I) or (II) (e.g., adamantanyl substituted with one or more substituents selected, independently from halogen, methyl, ethyl, propyl, or isopropyl, or 3-(1,1,2,3,3,3-hexafluoro-propyl)-adamantanyl) are likewise prepared.

Example 4: Characterization of Solid Form of Compound D

Compound D was isolated in solid form as described in Example 3. Compound D was analyzed by X-ray powder diffraction (XRPD) analysis as well as by dynamic vapor sorption (DVS) analysis. The isolated solid form of Compound D was observed to be amorphous by XRPD and prone to deliquescence, e.g., it was hygroscopic as observed by gravimetric vapor sorption (GVS) kinetic plotting. The isolated solid form of Compound D had a melting point range of 160-165° C.

Example 5: Synthesis of Compound 1 (4-((S)-3-amino-1-(isoquinolin-6-ylamino)-1-oxopropan-2-yl) benzyl adamantane-1-carboxylate)

FIG. 3 and FIG. 4 depict synthetic schemes for preparing Compound 1.

To 4-((S)-3-amino-1-(isoquinolin-6-ylamino)-1-oxopropan-2-yl)benzyl adamantane-1-carboxylate dimesylate (7.2 g) was added deionized water (96 mL) to dissolve. Then $KHCO_3$ (10%, 72 mL) was added to precipitate the material, which was extracted with dichloromethane (270 mL combined extractions) until TLC (thin layer chromatography) indicated all the compound was out of the aqueous layer and in the dichloromethane. The combined fractions were dried ($Na_2SO_4$), filtered and evaporated. Automated column chromatography (Teledyne, 40 g) 0-15% MeOH: 2N $NH_3$-MeOH (1:1): dichloromethane provided pure 4-((S)-3-amino-1-(isoquinolin-6-ylamino)-1-oxopropan-2-yl)benzyl adamantane-1-carboxylate (3.82 g, 75%).

The corresponding 2-adamantanyl compound is similarly prepared. Similarly, other 1- or 2-adamantanyl compounds of formulae (I) or (II) (e.g., adamantanyl substituted with one or more substituents selected, independently from halogen, methyl, ethyl, propyl, or isopropyl, or 3-(1,1,2,3,3,3-hexafluoro-propyl)-adamantanyl) are likewise prepared.

Example 6: General Synthesis of Salt Forms

To 4-((S)-3-amino-1-(isoquinolin-6-ylamino)-1-oxopropan-2-yl)benzyl adamantane-1-carboxylate (277 mg, 0.57 mmol) in DCM (dichloromethane) (2.5 mL) cooled to 0° C. was added methanesulfonic acid (37.1 mL, 0.57 mmol) and the solution was warmed to room temperature, stirred for 20 minutes then evaporated and dried on the high vacuum to give pure 4-((S)-3-amino-1-(isoquinolin-6-ylamino)-1-oxopropan-2-yl)benzyl adamantane-1-carboxylate mono-methanesulfonate (238 mg, 72%). Salts of other adamantanyl compounds herein are similarly prepared.

The corresponding 2-adamantanyl compound is similarly prepared. Similarly, other monomesylate salts of 1- or 2-adamantanyl compounds of formulae (I) or (II) (e.g., adamantanyl substituted with one or more substituents selected, independently from halogen, methyl, ethyl, propyl, or isopropyl, or 3-(1,1,2,3,3,3-hexafluoro-propyl)-adamantanyl) are likewise prepared. Other mono-salts of compounds of formulae (I) or (II) are similarly prepared using 1 molar equivalent of corresponding acid. Di-salts of compounds of formulae (I) or (II) are similarly prepared using 2 to 2.5 molar equivalents of corresponding acid.

Example 7: Solubility of Salt Forms

The compounds were charged to target 5 mg/mL in deionized water to supersaturated solutions and the pH was obtained. The samples were then spun down by centrifugation and the supernatant was tested for solubility (aqueous solubility, mg/mL) in deionized water using HPLC. The di-MsOH and the di-HCl did not reach saturation at 5 mg/ml in deionized water, (pHs 3.3-3.4), therefore the pHs of the di-MsOH and the di-HCl were adjusted to pH 5.7 and solubilities at pH 5.7 were obtained.

Certain salt forms prepared are shown in Table 1 and include melting point ranges as well as aqueous solubility values that were determined by standard techniques.

TABLE 1

Mono- and Di-Salt Forms of Compound 1.

| Salt | MW salt | Mp | Aq. Solubility (mg/mL) In DI $H_2O$ | pH (22.0° C.) |
|---|---|---|---|---|
| Free base (Compound 1) | 483.6 | 80-87° C. | 0.0021 | 5.73 |
| diMsOH (Compound D) | 675.8 | 160-165° C. | 0.1859 (>5 mg/mL at pH 3.40) | 5.74* (Initial pH 3.40) |

TABLE 1-continued

| Mono- and Di-Salt Forms of Compound 1. | | | | |
|---|---|---|---|---|
| Salt | MW salt | Mp | Aq. Solubility (mg/mL) In DI $H_2O$ | pH (22.0° C.) |
| MsOH | 579.7 | 166-170° C. | 4.0212 | 5.93 |
| diHCl | 556.5 | 215-222° C. | 0.1558 (>5 mg/mL at pH 3.45) | 5.73* (Initial pH 3.45) |
| HCl | 520.1 | 157-158° C. | 2.3393 | 5.82 |
| Tosylate | 655.8 | 205-210° C. | 0.0718 | 5.68 |
| Maleate | 599.6 | 162-169° C. | 0.3356 | 4.36 |
| Fumarate | 599.6 | 180-184° C. | 0.4647 | 4.15 |
| Citrate | 675.7 | 173-176° C. | 0.0894 | 4.57 |

*Samples were not saturated at the initial pH and pH was increased with 1N NaOH to obtain the supersaturated solution.

Example 8: Kinase Inhibition Assays

All compounds are initially prepared as 10 mM stocks in anhydrous dimethylsulfoxide (DMSO). A 20 μL aliquot of the 10 mM solutions is transferred to individual wells in column 1 of a 96-well polypropylene microtiter plate (Corning #3363) and diluted with DMSO to give a final compound concentration of 4 mM. Test compounds are then serially diluted 1:5 in DMSO for an 11-point concentration response and further diluted in the assay buffer bringing all compound concentrations to a final range of 100 μM to 10 μM in 2.5% DMSO. The assay is performed in white 96-well, flat-bottom, half-area, non-binding assay plate (Corning #3642) in assay buffer consisting of 20 mM HEPES (pH 7.5), 10 mM $MgCl_2$*$6H_2O$, 100 μM sodium orthovanadate, 0.05% CHAPS and 0.1% bovine serum albumin. A 10 μL aliquot of compound from each well of the intermediate dilution plate and 20 μL of a 2× substrate/enzyme solution containing acceptor substrate (800 nM RSK2 peptide 10-mer having a MW of 1242.5, e.g., product number SRP0687 from Sigma-Aldrich), ROCK2 enzyme (10 nM), or ROCK1 enzyme, or PKA enzyme (10 nM; protein kinase A), or PKN2 (10 nM; PKC-related serine/threonine protein kinase), or MRCKa (10 nM; myotonic dystrophy kinase-related CDC42-binding kinase alpha), and 1,4-Dithiothreitol (DTT, 2 μM) are added to all wells. The reaction is initiated by the addition of 10 μL of 4× stock solution ATP (2 μM). Reactions are thoroughly mixed manually, covered, and allowed to incubate at room temperature for 75 min. Protein kinase activity is quantitated using Promega's KINASE-GLOTM luminescent Kinase Assay Kit according to the manufacturer's directions. ATP concentrations remaining in Test wells following the termination of the enzymatic reaction are compared against control wells containing equivalent amounts of DMSO containing no inhibitor (CTRL). ATP concentrations in both Test wells and CTRL wells are normalized against background (BKG) ATP concentrations in wells containing concentrations of inhibitor that completely inhibited the protein kinase under investigation (i.e. a concentration that prevented any consumption of ATP over the course of the incubation). Percent of Control (POC) values are determined for each concentration of compound tested according to the equation:

$$POC = ((\text{Test well value} - BKG)/(CTRL - BKG)) * 100$$

$IC_{50}$ values are calculated using the following 4-parameter logistic curve-fitting algorithm:

$$f(x) = (A + ((B - A)/(1 + ((x/C)^\wedge D))))$$

$IC_{50}$ values are converted to K values using the following Cheng-Prusoff Equation:

$$K_i = IC_{50}/(1 + ([ATP]/KmATP])).$$

Adamantanyl compounds herein assayed inhibit the assayed kinase at commercially or therapeutically relevant levels. Specific results are shown in Table 2.

TABLE 2

| $K_i$ (nM) of compounds. | | | | | |
|---|---|---|---|---|---|
| Compound | ROCK2 | ROCK1 | PKA | PKN2 | MRCKa |
| 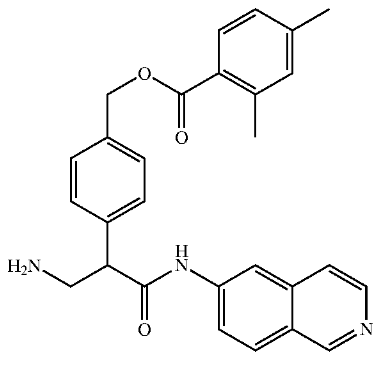 [SMILES: Cc1ccc(C(=O)OCc2ccc(C(CN)C(=O)Nc3ccc4cnccc4c3)cc2)c(C)c1] Di-mesylate | 2.3 | 3 | 11 | 5 | 282 |

TABLE 2-continued
| Ki (nM) of compounds. | | | | | |
|---|---|---|---|---|---|
| Compound | ROCK2 | ROCK1 | PKA | PKN2 | MRCKa |
| 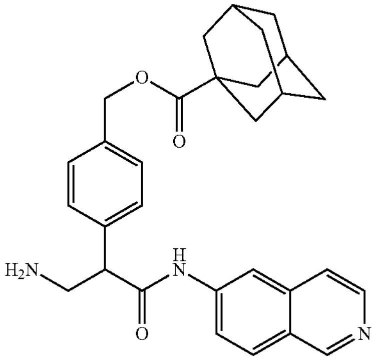 Di-mesylate | 18.8, 21.7 | 4.5 (n =1) | 110 | 8 | 1483 |
| 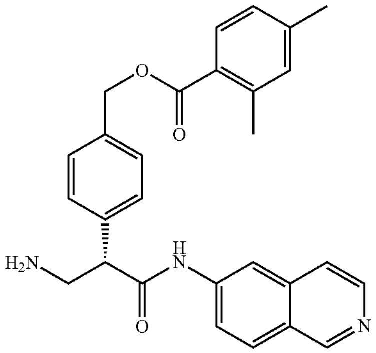 [SMILES: Cc1ccc(C(=O)OCc2ccc([C@@H](CN)C(=O)Nc3ccc4cnccc4c3)cc2)c(C)c1] Di-mesylate (Compound E) | 1.1 | 1.2 | 5 | 3 | 129 |
| 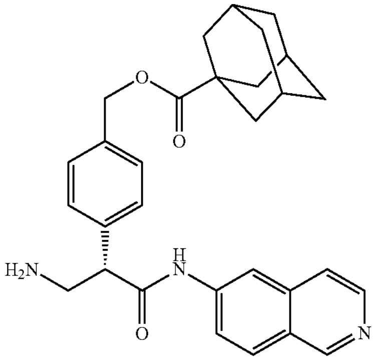 Di-mesylate (Compound D) | 9.8, 7.9 | | | | |
| 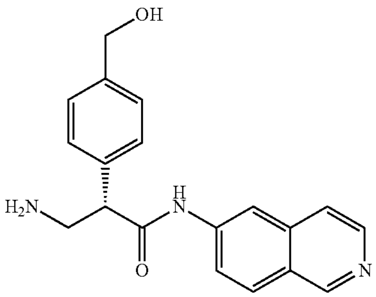 Free base (Compound 3) | 0.2 | 0.2 | 1 | 1 | 7 |

TABLE 2-continued
| Ki (nM) of compounds. | | | | | |
|---|---|---|---|---|---|
| Compound | ROCK2 | ROCK1 | PKA | PKN2 | MRCKa |
| 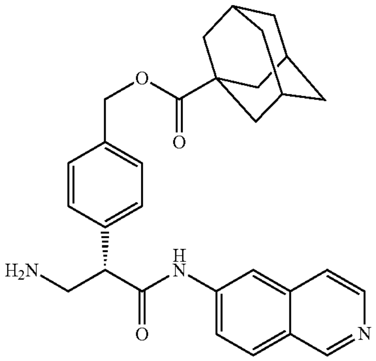 Free base (Compound 1) | 3.5 | | | | |
| 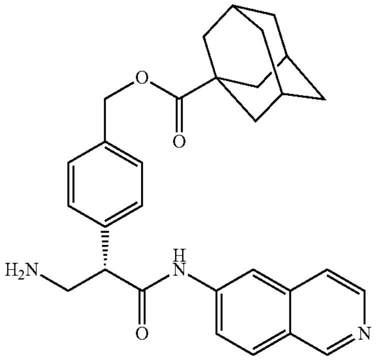 Mono-Mesylate | 6.4 | | | | |
| 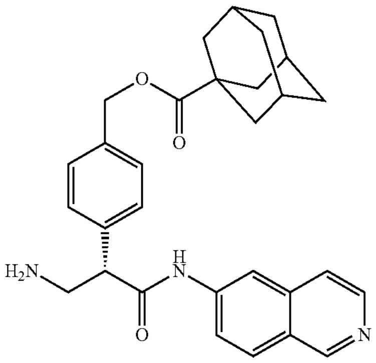 Di-HCl | 8.9 | | | | |

TABLE 2-continued
| Ki (nM) of compounds. | | | | | |
|---|---|---|---|---|---|
| Compound | ROCK2 | ROCK1 | PKA | PKN2 | MRCKa |
| 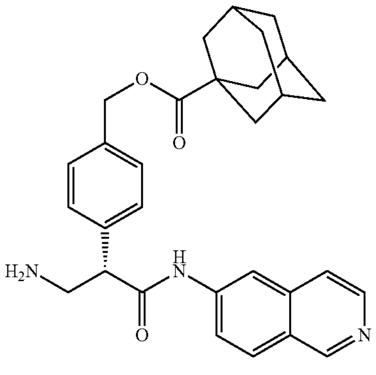 Mono-HCl | 6.9 | | | | |
| 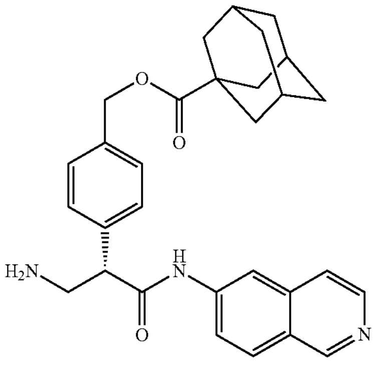 Mono-Tosylate | 3.9 | | | | |
| 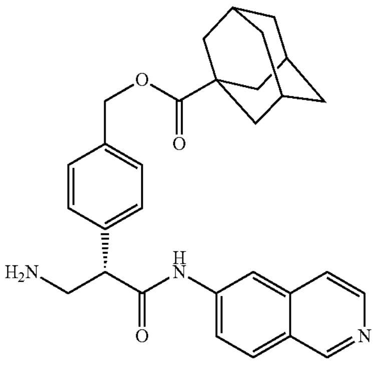 Mono-Maleate | 4.9 | | | | |

TABLE 2-continued

| Ki (nM) of compounds. | | | | | |
|---|---|---|---|---|---|
| Compound | ROCK2 | ROCK1 | PKA | PKN2 | MRCKa |
| 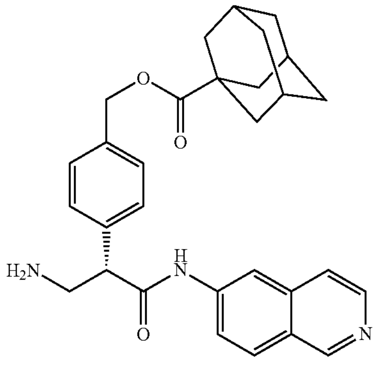 Mono-Fumarate | 5.7 | | | | |
| 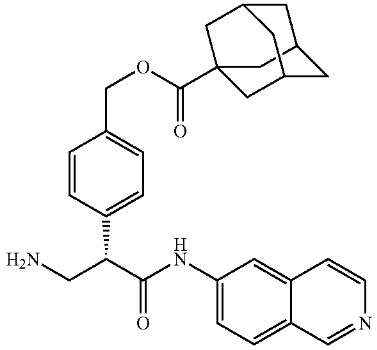 Mono-Citrate | 7.2 | | | | |

Example 9: Corneal Metabolism, Corneal Binding, and Hydrolysis

200 μM aqueous solutions of individual ROCK inhibitor compounds were assayed for compound stability after the addition of corneal tissue by measuring loss of the compound from solution over time, including loss due to binding of the intact compound to the corneal tissue (propensity for tissue entrapment). Specific results are shown in Table 3. Compounds were prepared analogous to the synthetic procedures described herein, or analogous to synthetic procedures described in U.S. Pat. No. 8,394,826, the content of which is incorporated herein by reference.

Intact globes were harvested from rabbit (Dutch Belted, Robinson Services, Inc., Mockesville, NC), stored in K-Sol corneal preservation buffer under cold conditions, and used within 24 hours of sacrifice. Human corneas were harvested and preserved according to current tissue banking procedures. Human corneal tissues acquired were viable but rejected for transplant due only to serological incompatibility.

Due to the size difference of corneas between species, corneal tissue punches of various sizes were used for the corneal metabolism assays as follows: 7 mm in diameter circular punches (surface area of 39 $mm^2$) for human (n=3) corneas; and 9 mm o.d.×5 mm i.d. ring punches (surface areas of 44 $mm^2$) for rabbit cornea (n=3). The weights of the corneal punches were approximately the same for human and rabbit corneal punches. Corneal punches were stored in phosphate buffered saline (#21-040-CV, Mediatech Inc., Herndon, VA) and used within one hour of preparation.

Test article was prepared at a concentration of 400 μM by dissolving netarsudil in a solution containing 4.7% D-mannitol and 0.05% boric acid at pH 6.5. Assays were performed in 96-well deep-well polypropylene plates (Corning Costar #3961, Lowell, MA). Corneal tissues were transferred to wells containing 1 mL of mannitol/boric acid buffer. The 96-well plate and the 400 μM test article solutions were preheated in a 37° C. water bath for 15 minutes. Reactions were initiated by adding 1 mL of 400 μM test article to wells containing corneal tissues in 1 mL buffer followed by thorough trituration, yielding a final incubation concentration of 200 μM. Reactions were terminated at appropriate time intervals by transferring a 100 μL aliquot of solution from the well containing corneal tissue to an equal volume of cold acetonitrile followed by thorough trituration. The samples were centrifuged at 10,000×g for 10 min and the supernatants were subsequently transferred to HPLC vials for analysis. Samples were analyzed by HPLC using a Waters Alliance 2695 HPLC (Milford, MA) equipped with a Symmetry C18 4.6×75 mm 3.5 μm column. Peak areas were integrated using Mass Lynx V4 (Waters Corporation, Milford, MA).

Loss of Compound E from solution after a 4-hour incubation with human corneal tissue ranged from 23.4% to 31.4%, with approximately half of the loss due to binding of intact compound to the corneal tissue. The proportion of Compound E lost to corneal biding was larger when Compound E was incubated with rabbit corneal tissue. In contrast, two compounds, (S)-4-(3-amino-1-(isoquinolin-6-ylamino)-1-oxopropan-2-yl)benzyl glycinate and(S)-4-(3-amino-1-(isoquinolin-6-ylamino)-1-oxopropan-2-yl)benzyl butyrate, showed equal or greater loss of the parent compound over time than Compound E with little or no corneal binding. However, unlike Compound E which has acceptable stability when stored in aqueous solution, the two compounds were unstable in aqueous solution due to a high rate of spontaneous ester hydrolysis.

TABLE 3

Compound Stability in Presence of Corneal Tissue.

| 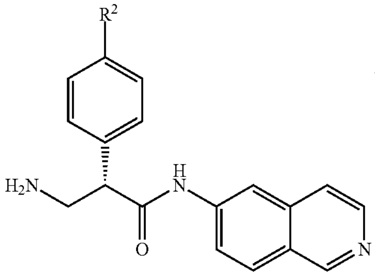 Di-mesylate | % compound loss @ 4 hr (including loss to corneal binding) | % compound bound to corneal tissue @ 4 hr | % compound loss @ 4 hr excluding corneal binding |
|---|---|---|---|
| 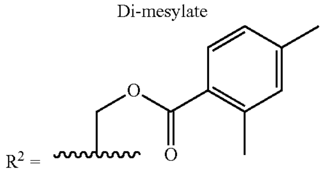 Compound E | 23.4, 25.5, 26.0, 26.9, 29.2, 31.4 (human) 33.2 (rabbit) | 11.3, 13.1, 13.3, 13.7, 14.7, 15.7 (human) 20.6 (rabbit) | 12.1, 12.4, 12.7, 13.2, 14.5, 15.7 (human) 12.6 (rabbit) |
| 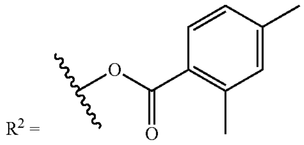 [SMILES: *OC(=O)c1ccc(C)cc1C] | 20.7 (human) | 13.0 (human) | 7.7 (human) |
| 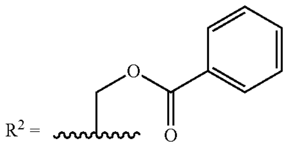 [SMILES: *COC(=O)c1ccccc1] | 24.7 (human) | 13.7 (human) | 11.0 (human) |
| 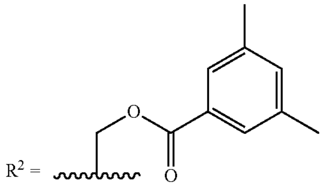 [SMILES: *COC(=O)c1cc(C)cc(C)c1] | 26.3 (human) | 13.5 (human) | 12.8 (human) |
| 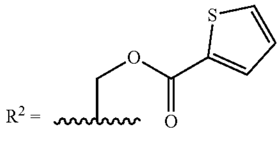 [SMILES: *COC(=O)c1cccs1] | 24.6 (human) | 11.4 (human) | 13.2 (human) |
| 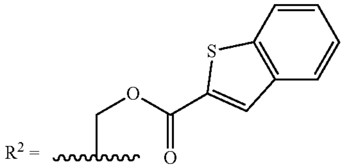 [SMILES: *COC(=O)c1cc2ccccc2s1] | 23.3 (human) | 12.8 (human) | 10.5 (human) |
| 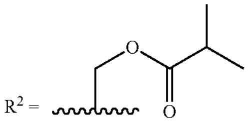 [SMILES: *COC(=O)C(C)C] | 9.1 (human) | 4.6 (human) | 4.5 (human) |

TABLE 3-continued

| Compound Stability in Presence of Corneal Tissue. | | | |
|---|---|---|---|
| 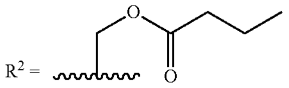 [SMILES: *COC(=O)CCC] | 25.7 (rabbit)<br>18.8 (human) | 0.3 (rabbit)<br>6.2 (human) | 25.4 (rabbit)<br>13.6 (human) |
| 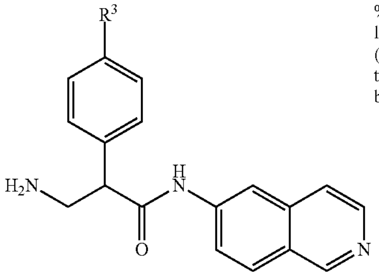 | % compound loss @ 4 hr (including loss to corneal binding) | % compound bound to corneal tissue @ 4 hr | % compound loss @ 4 hr excluding corneal binding |
| 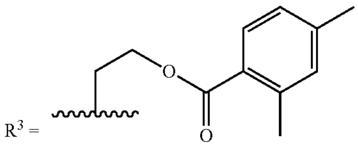 [SMILES: *CCOC(=O)c1ccc(C)cc1C] | 23.2 (human) | 14.8 (human) | 8.4 (human) |
| 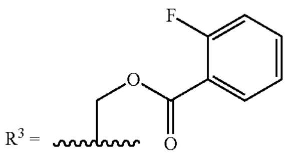 [SMILES: *COC(=O)c1ccccc1F] | 23.7 (human) | 15.5 (human) | 8.2 (human) |
| 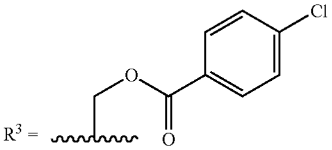 [SMILES: *COC(=O)c1ccc(Cl)cc1] | 27.2 (human) | 14.4 (human) | 12.8 (human) |
| 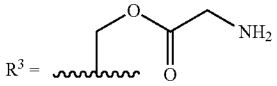 | 60.2 (human) | 0.0 (human) | 60.2 (human) |

Example 10: Conjunctival Clearance

Figure 5:
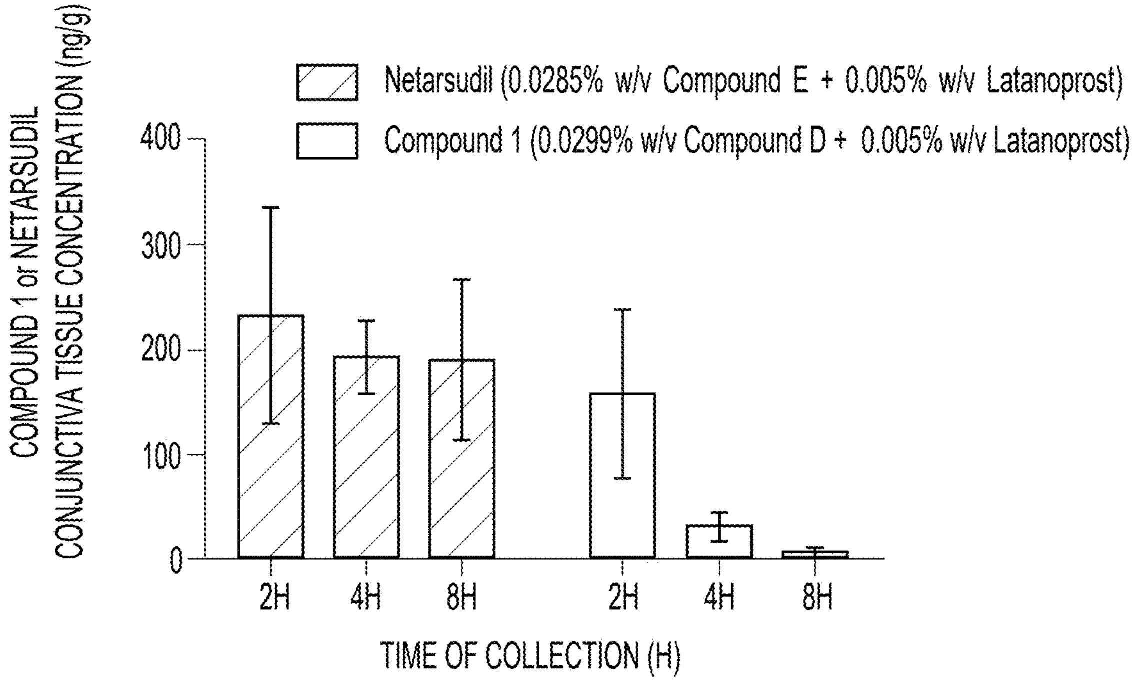
FIG. 5 depicts changes over time of the concentration of Compound D or Compound E in conjunctiva tissue following ocular instillation of fixed dose combinations of Compound D with latanoprost or Compound E with latanoprost. 0.0285% w/v Compound E corresponds to 0.02% w/v netarsudil (i.e. as the free base). 0.0299% w/v Compound D corresponds to 0.02% w/v Compound 1.

A solution of 0.0299% w/v Compound D was prepared (0.02% w/v based on free base, i.e. Compound 1) at pH 5 with latanoprost (0.005% w/v), dosed topically to rabbit eyes and assayed for clearance from conjunctiva, which was compared to a solution of 0.0285% w/v Compound E (0.02% w/v based on free base, i.e. netarsudil) at pH 5 with latanoprost (0.005% w/v). Data are depicted in FIG. 5 and show that Compound 1 demonstrates faster clearance from the conjunctiva than netarsudil. In a specific example both eyes are dosed topical ocular once daily, in the morning, for 4 days using droptainer prior to tissue collection. 2, 4, and 8 hours after last installation of dosing solution rabbits are euthanized and conjunctiva is collected for drug concentration analysis using LCMS methods. Following tissue weight collection tissues are stored at −80° C. until extractions occur and analysis for drug concentration levels are performed using LCMS.

Example 11: Intraocular Pressure (IOP) Reduction and Hyperemia Scoring

Solutions of ROCK inhibitor compounds herein are prepared and assayed in rabbits to determine their capacity to reduce intraocular pressure. (S)-3-amino-2-(4-(hydroxymethyl)phenyl)-N-(isoquinolin-6-yl) propenamide (netarsudil metabolite; Compound 3) was purchased or prepared analogous to the synthetic procedures described herein (e.g., combining the synthetic schemes of FIG. 1 and FIG. 4), or analogous to synthetic procedures described in U.S. Pat. No. 8,394,826, the content of which is incorporated herein by reference.

In a specific example, rabbits were dosed once daily for four consecutive days with either(S)-3-amino-2-(4-(hydroxymethyl)phenyl)-N-(isoquinolin-6-yl) propenamide (Compound 3) (0.04% w/v solution based on free base, pH 5, 0.05% w/v boric acid, 4.7% w/v mannitol, 0.02% w/v benzalkonium chloride) or Compound E (0.04% w/v solution based on free base, pH 5, 0.05% w/v boric acid, 4.7% w/v mannitol, 0.02% w/v benzalkonium chloride). Dosing was only to the right eye (OD); the contralateral eye (OS) served as an internal control. Animals in each group (7 male adult (about 9 months old) Dutch belted rabbits per group) were dosed q.d. in the morning (between about 0600-0900 hours) on Study Days 1-4. A single drop of proparacaine (0.05%) was applied to each eye prior to measuring IOP with a pneumotonometer (Reichert Model 30). IOP measurements were collected in triplicate for each eye at pre-dose and at 2-, 4-, and 8-hours post dose on Days 1, 2, 3, and 4. IOP data were reported as the mean of the three measurements at each timepoint and as the difference in IOP between the treated (OD) and untreated (OS) eyes. The OS eyes served as a control for diurnal fluctuations in IOP. Photographic images of eyes were collected at each time point to score ocular tolerability.

Figure 6:
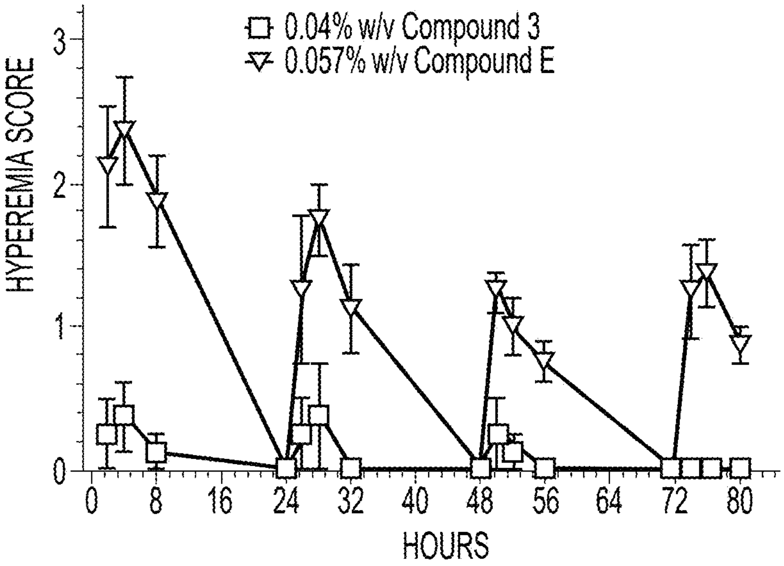
FIG. 6 depicts changes over time of hyperemia scores following once-daily ocular instillation of(S)-3-amino-2-(4-(hydroxymethyl)phenyl)-N-(isoquinolin-6-yl) propenamide (Compound 3) or Compound E. 0.057% w/v Compound E corresponds to 0.04% w/v netarsudil.
Figure 7:
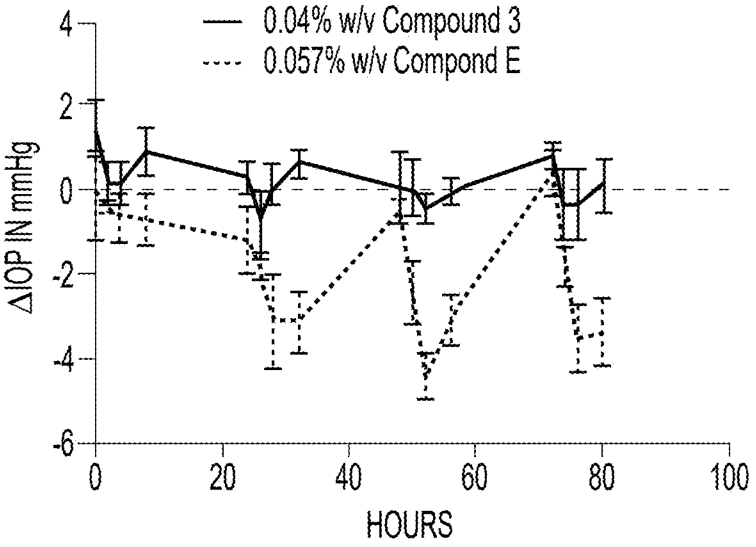
FIG. 7 depicts changes over time of intraocular pressure following once-daily ocular instillation of(S)-3-amino-2-(4-(hydroxymethyl)phenyl)-N-(isoquinolin-6-yl) propenamide (Compound 3) or Compound E.

Remarkably, Compound 3, the active metabolite of netarsudil, was observed to cause neither hyperemia (FIG. 6) nor lower IOP (FIG. 7) when dosed topically in rabbits despite its sub-nanomolar ROCK1 activity, whereas hyperemia and IOP reduction were both observed with Compound E. Based on the observation that topical administration of the active metabolite fails to produce hyperemia, it has been found that netarsudil-induced conjunctival hyperemia is caused primarily by netarsudil, not its active metabolite. Further, observing that administration of the active metabolite failed to reduce IOP, the results demonstrate it is necessary to develop prodrugs of the active metabolite that can transit the ocular surface to allow the active metabolite to reach the target tissue for IOP reduction. Without being bound by theory, it is thought that prodrugs that are converted to the active metabolite more rapidly in the conjunctiva and cornea than netarsudil could reduce the duration of conjunctival hyperemia as compared to netarsudil, while also maintaining the ability to reduce IOP.

Figure 8:
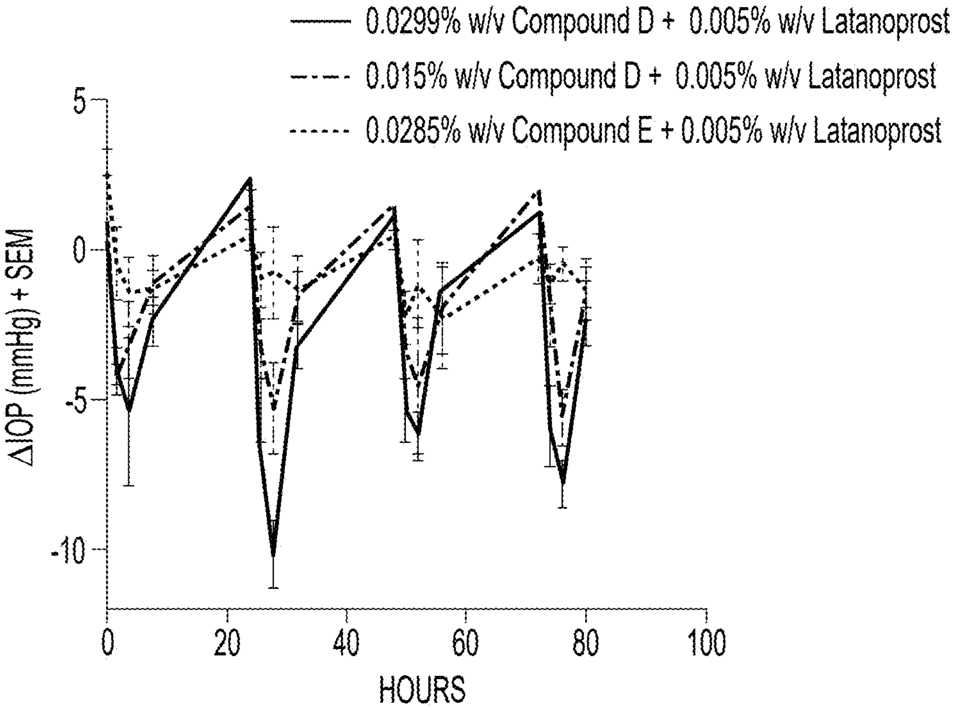
FIG. 8 depicts changes over time of intraocular pressure following once-daily ocular instillation of fixed dose combinations of Compound D with latanoprost or Compound E with latanoprost. 0.015% w/v Compound D corresponds to 0.01% w/v Compound 1.
Figure 9:
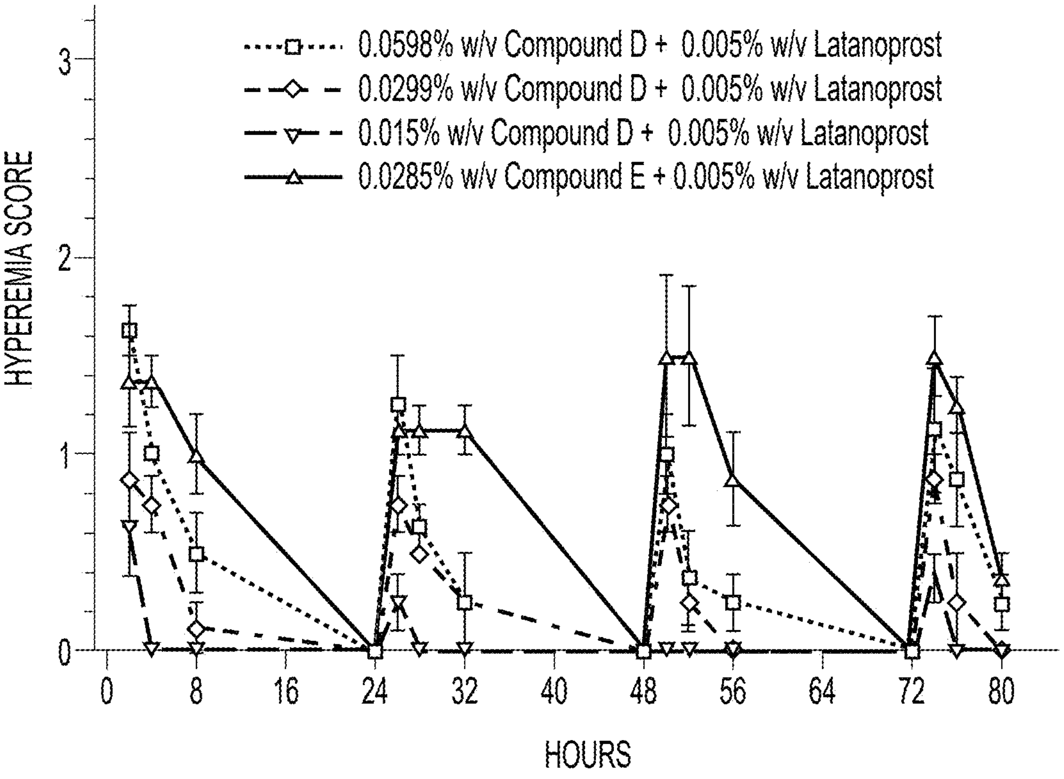
FIG. 9 depicts changes over time of hyperemia scores following once-daily ocular instillation of fixed dose combinations of Compound D with latanoprost or Compound E with latanoprost. 0.0598% w/v Compound D corresponds to 0.04% w/v Compound 1.

Rabbits were also dosed once-daily for four days with a solution of Compound D (0.01, 0.02, or 0.04% w/v based on free base, i.e. Compound 1) at pH 5 with latanoprost (0.005% w/v) and assayed for hyperemia and IOP reduction, which was compared to a solution of Compound E (0.02% w/v based on free base) at pH 5 with latanoprost (0.005% w/v). The Compound D solution exhibited comparable or better IOP reduction as compared to Compound E (FIG. 8), even when used at half the concentration (0.01% compared to 0.02%). Furthermore, the Compound D solution exhibited faster recovery from hyperemia as compared to Compound E (FIG. 9), even when used at twice the concentration (0.04% compared to 0.02%) after multiple days of administration.

Example 12: Ocular Tissue Distribution

Solutions of ROCK inhibitor compounds herein are prepared and assayed in rabbits to determine their distribution, as well as the distribution of their esterase metabolite, following ocular instillation. In a specific example, a solution of Compound D (0.02% w/v based on free base, i.e. Compound 1) at pH 5 with latanoprost (0.005% w/v) was prepared and administered as well as a solution of Compound E (0.02% w/v based on free base) at pH 5 with latanoprost (0.005% w/v). In a specific example both eyes are dosed topical ocular once daily, in the morning, for 4 days using a droptainer. 2, 4, and 8 hours after last installation of dosing solution rabbits are euthanized and conjunctiva is collected for drug concentration analysis using LCMS methods. Aqueous humor is collected after enucleation. Following this the whole globe is placed in a container on dry ice and allowed to freeze fully. Whole globes and accompanying tissues are kept at −80° C. until dissection. Dissections are performed using tools cleaned with methanol before and in between specimens. Following dissection and tissue weight collections tissues are stored at −80° C. until extractions occur and analysis for drug concentration levels are performed using LCMS.

Figure 10:
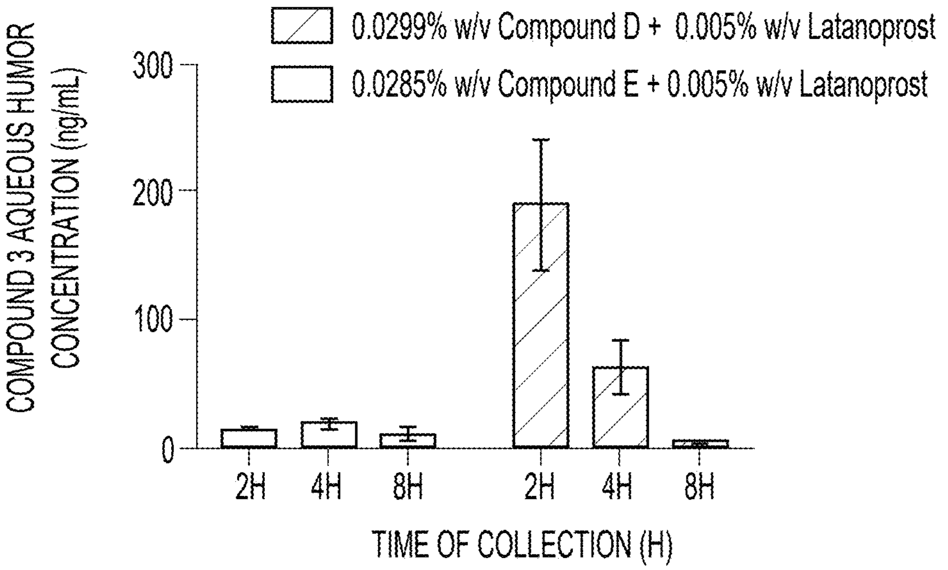
FIG. 10 depicts changes over time of the concentration of Compound 3 in aqueous humor following ocular instillation of fixed dose combinations of Compound D with latanoprost or Compound E with latanoprost.
Figure 11:
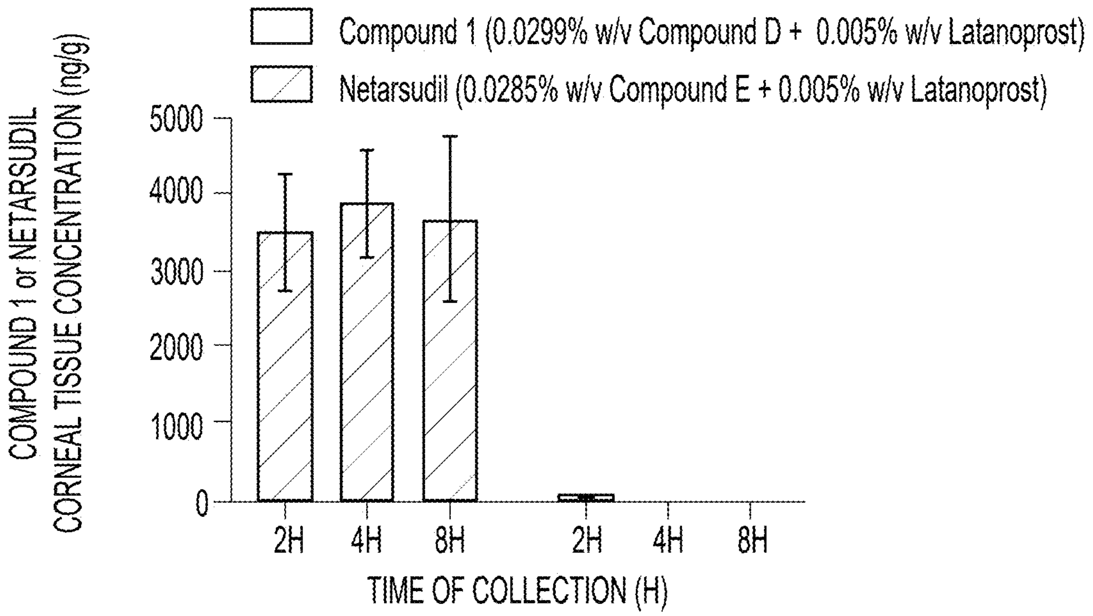
FIG. 11 depicts changes over time of the corneal tissue concentration of Compound 1 or netarsudil following ocular instillation of fixed dose combinations of Compound D with latanoprost or Compound E with latanoprost, respectively.

Higher levels of the active metabolite Compound 3 were observed in aqueous humor when Compound D was administered as compared to administration of Compound E (FIG. 10), which indicates Compound D was surprisingly more effective at effecting delivery of active metabolite to the aqueous humor than Compound E. Additionally, significantly lower levels of Compound 1 were detected in corneal tissue as compared to netarsudil (FIG. 11) suggesting improved metabolism of Compound 1 by corneal esterase, which conclusion is also supported by the results of Example 9. As shown in Example 11, ocular instillation of the active metabolite itself results in no hyperemia, which suggests that hyperemia is caused by the prodrugs of the metabolite. Thus, without being bound by theory, a reduced level of Compound 1 in the cornea relative to netarsudil could reduce the amount of Compound 1 that diffuses from the cornea back into the tear film relative to netarsudil, which in turn could produce less conjunctival hyperemia than netarsudil.

Example 13: Ocular Tolerability

A solution of Compound D was prepared (0.04% w/v based on free base, i.e. Compound 1) at pH 5 and assayed for acute ocular tolerability in rabbits following exaggerated daily dosing frequency (BID and QID, topical ocular) for 3 days, which was compared to a solution of Compound E (0.04% w/v based on free base) at pH 5. Vehicle and test articles (TAs) were administered topically to both eyes of each animal by eye dropper bottle (1 drop per eye) 2 (BID) to 4 (QID) times per day for 3 days. BID doses were administered 6-8 hours apart, and QID doses were administered 2-3 hours apart. Group 1 animals received vehicle QID. Group 2 received Compound E (0.04% w/v based on free base) BID. Group 3 received Compound D (0.04% w/v based on free base) BID. Group 4 received Compound E (0.04% w/v based on free base) QID. Group 5 received Compound D (0.04% w/v based on free base). Complete ocular examination (modified Hackett and McDonald) using a slit lamp biomicroscope and indirect ophthalmoscope to evaluate ocular surface morphology, anterior segment and posterior segment inflammation, cataract formation, and retinal changes was conducted by a board-certified veterinary ophthalmologist who was masked to the identity of the rabbits during each examination. Ocular examinations were performed at baseline and on Day 3 following the completion of dosing. Inflammation was scored as follows: 0=no inflammation; 1-4=mild inflammation; 5-10=moderate inflammation; 11+=severe inflammation.

Figure 12:
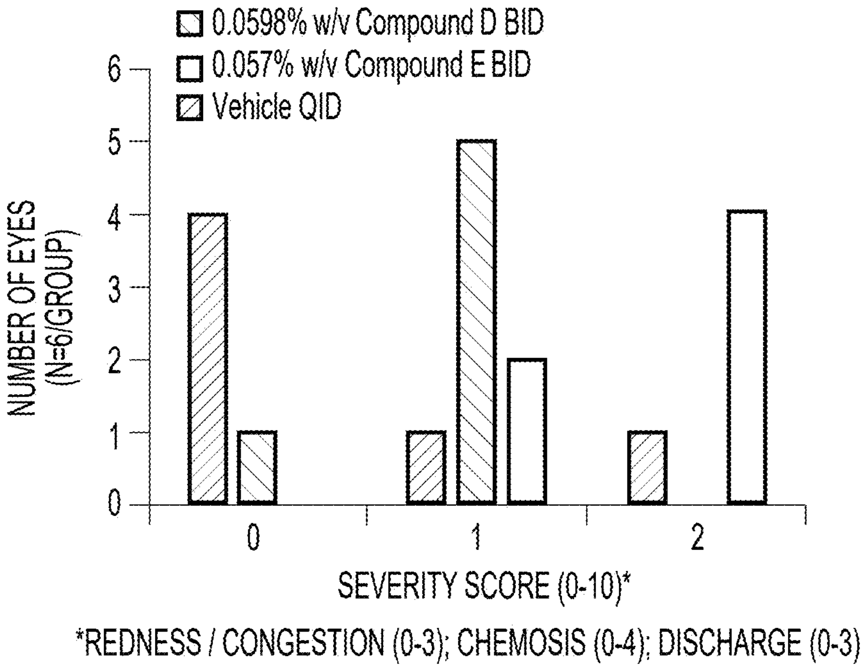
FIG. 12 depicts ocular tolerability, as scored by total conjunctival ocular exam severity score, of a population of subjects (rabbits) administered Compound D or Compound E by ocular instillation. Adverse findings in the conjunctiva could include redness/congestion, chemosis, and/or discharge.

QID dosing of Compound E (0.04% w/v based on free base) in Group 4 was suspended on Day 2 after the third dose due to the severity of ocular inflammation observed. By contrast, animals dosed with Compound D tolerated the full 3 days of QID dosing. Tolerability scores for BID dosing are depicted in FIG. 12. Compound D was better tolerated than Compound E when dosed BID.

Example 14: Ex Vivo Corneal Metabolism of ROCK1 Compounds

The purpose of this study was to characterize the metabolism of the ROCK1 compounds Compound 1 (administered as its dimesylate salt, Compound D) and netarsudil (administered as its dimesylate salt, Compound E) in ex vivo pig cornea tissue by monitoring the disappearance of parent compound and the formation of the active esterase metabolite, Compound 3, over time. Both compounds are metabolized (e.g., hydrolized) at an ester bond to form Compound 3.

SUMMARY

Ex vivo corneal metabolism studies were used to characterize the metabolism of the Rho kinase inhibitor (ROCK1) Compound 1 in comparison to netarsudil. Both compounds (as dimesylate salts) were incubated with pig corneal tissue explants ex vivo over a 4-hour study period. Disappearance of each compound from the incubation medium was monitored as well as formation of the active esterase metabolite, Compound 3. At the end of 4 hours, the ex vivo corneal tissue was analyzed for binding of Compound 1, netarsudil, and the active metabolite, Compound 3.

Compound 1 and netarsudil exhibited comparable rates of disappearance over the 4-hour study period with 48% and 56%, respectively, of the starting compound concentrations remaining. Appreciable concentrations of both compounds remained associated with the corneal tissue at the end of the study, therefore, disappearance of both compounds was attributable to 1) ester hydrolysis to the active metabolite and 2) binding to the cornea tissue. A greater amount of netarsudil, 39%, was bound to cornea compared with 25% of Compound 1, suggesting a potentially higher binding avidity of netarsudil for the cornea or higher sequestration in the tissue. There was a surprising difference between the two compounds regarding formation of the metabolite Compound 3. Esterase hydrolysis of Compound 1 generated much higher levels, about an order of magnitude greater, of Compound 3 in solution (45%) than hydrolysis of netarsudil (4%). At the end of the study, levels of Compound 3 bound to cornea were also higher, about twice as much, following incubation with Compound 1 (3.7%) than after incubation with netarsudil (1.6%). Hydrolysis of Compound 1 resulted in a formation rate of total Compound 3 (metabolite in solution+bound to cornea) of 49±8 nmol/4 hours compared to a metabolite formation from hydrolysis of netarsudil of 5±3 nmol/4 hours.

Preparation of Test Article Stock Solutions:

Compound D and Compound E were prepared as 100 μM stock solutions in 0.05% boric acid, 4.7% D-mannitol (BAM) at pH 6.5.

Study Design and Procedure:

One mL of BAM at pH 6.5 was added to selected wells of a 24-well plate. Corneal tissue was dissected from the pig eye of four different animals and a 5 mm punch removed using up to 4 punches per cornea. Corneal punches from each animal were distributed equally across the tested compounds so that each compound was evaluated with a corneal punch from each of the four animals (n=4).

The well plate with corneal punches as well as the compound solutions were stored at 37° C. for 15 minutes in an incubator to equilibrate all media. After 15 minutes, the well plate and solutions were removed from the incubator. To initiate the reaction process, 1 mL of each 100 μM test article solution was added to each of 4 wells. A control well was also prepared under the same conditions with no corneal tissue present to monitor for tissue independent degradation of the parent test articles over the course of the experiment. The final concentration of each test article in the assay was 50 μM.

The plate was then placed on a shaker in an incubator at 37° C. and slowly rotated at 50 rpm for the duration of the study. To evaluate compound metabolism, aliquots (100 μL) were pulled at initial (t=0), 30, 60, 90, 120, 180, and 240 minutes including for the control samples. At each time-point, a 100 μL aliquot of sample was added to a 1.5 mL Eppendorf tube containing 100 μL of cold acetonitrile (ACN)/0.1% formic acid. Each metabolism sample was vortexed and stored frozen until analyzed.

At the end of the 4-hour study, each cornea punch was recovered, lightly dried with a Kimwipe, placed in pre-weighed bead mill tubes (Fisherbrand), and weighed to determine the corneal tissue weights. To each corneal tissue sample, 100 μL of cold ACN/0.1% formic acid was added and the samples stored frozen until analysis.

Metabolism Samples Preparation:

Metabolic samples for analysis were generated as described above in two independent experiments each consisting of four analytical samples per timepoint per compound.

The 200 μL metabolism samples were centrifuged prior to additional dilution. From the centrifuged portion, 100 μL was diluted to 1 mL with 0.1% formic acid in methanol (Diluent).

Test article stock solutions used for the study were also analyzed for initial content. These were prepared by transferring 125 μL into 1.0 mL of Diluent.

Corneal Tissue Samples Preparation:

Each cornea punch was homogenized in bead mill tubes with 100 μL of ACN/0.1% formic acid. Samples were homogenized with 3 cycles of milling using a Bead Mill 24 homogenizer and then diluted with 0.9 mL of 0.1% formic acid in ACN. The diluted sample was centrifuged prior to analysis.

Standards Preparation:

Samples were quantified from a single point standard of their respective test articles, Compound 1 and netarsudil as well as a standard of Compound 3. The analytical range for Compound 1, netarsudil, and Compound 3 was 0.05 ng/mL to 200 ng/ml and all standards were prepared in diluent. Along with the respective analytical standard, a combined internal standard (IS) consisting of deuterated internal standards of Compound 1, netarsudil, and Compound 3 was prepared at 3 ng/ml and used for LC-MS/MS analysis. A combined quality control (QC) standard for Compound 1, netarsudil, and Compound 3 was prepared at four different concentrations (150 ng/ml, 15 ng/ml, 1.5 ng/ml, and 0.15 ng/ml) to validate the assay conditions throughout the analysis.

Sample Analysis:

A 100 μL volume of the metabolism samples prepared above and a 100 μL volume of the corneal tissue samples prepared above were transferred into a new 96 well plate. In addition, 100 μL of standards and QCs (prepared above) and diluent blank samples were transferred to the same plate. To each well, 100 μL of internal standard was added followed by 300 μL of acetonitrile. Sample plate was capped, vortexed at 600 rpm for 1 minute followed by centrifugation at 3500 rpm for 10 min. Supernatant was transferred to a new 96 well plate and analyzed using LC-MS/MS.

Chromatographic Conditions:

The chromatographic conditions used for analysis are listed in Table 4. Samples were bracketed by standards and QCs throughout the LC-MS/MS run.

TABLE 4

LC-MS/MS Chromatographic Conditions for Analysis Metabolism Samples

| | |
|---|---|
| Column | Waters Xselect T3, 3 × 50 mm, 3.5 μm |
| Column Temp | 40° C. |
| Injection Volume | 2 μL |
| Flow Rate | 0.5 mL/min |

TABLE 4-continued

| LC-MS/MS Chromatographic Conditions for Analysis Metabolism Samples | | | |
|---|---|---|---|
| Mobile Phase | 0.1% Formic acid in water (A)<br>0.1% Formic acid in Acetonitrile (ACN) | | |
| | Time | % A | % B |
| Gradient | 0.0 | 100 | 0 |
| | 0.5 | 100 | 0 |
| | 2.00 | 0 | 100 |
| | 3.00 | 50 | 50 |
| | 4 | 100 | 0 |
| Run Time | 4 min | | |
| Mass Spec Source Parameters | Ion Source: HESI<br>Desolvation gas flow: 450<br>Desolvation temperature: 900 | | |

Study Results:

Compound 1 and netarsudil were incubated ex vivo with pig corneal tissue to characterize metabolism of the compounds by corneal esterases. In this study, the change in compound concentration over time was tracked as well as the increase in the esterase metabolite, Compound 3. The amount of each compound bound to corneal tissue, of each administered compound and Compound 3, at the end of the incubation was also determined.

In this study, Compound 1 and netarsudil exhibited comparable rates of disappearance over the 4-hour study period with 48% and 56%, respectively, of the starting prodrug concentrations remaining at 4 hours (Table 5). Appreciable concentrations of both prodrugs remained associated with the corneal tissue at the end of the study, therefore, disappearance of both prodrugs was attributable to 1) ester hydrolysis to the active metabolite and 2) binding to the cornea tissue. A greater amount of netarsudil, 39% of initially administered compound, was bound to cornea compared with 25% of Compound 1 (Table 6). There was a striking difference between the two administered compounds regarding formation of Compound 3. Esterase hydrolysis of Compound 1 generated much higher levels of Compound 3 in solution (45% of initially administered compound) than hydrolysis of netarsudil (4% of initially administered compound) (Table 5). At the end of the study, levels of Compound 3 bound to cornea were also slightly higher from Compound 1 (3.6% of initially administered compound) than from netarsudil (1.6% of initially administered compound) (Table 7). Metabolism of Compound 1 resulted in a formation rate of total Compound 3 (metabolite in solution+bound to cornea) of 49±8 nmol/4 hours compared to a metabolite formation from ester hydrolysis of netarsudil of 5±3 nmol/4 hours. No significant degradation of the two prodrugs in the absence of corneal tissue was observed.

Conclusions

An ex vivo corneal metabolism study was used to assess the metabolism and corneal binding of Compound 1 in comparison to netarsudil. Ester cleavage of both prodrugs generates the common active metabolite, Compound 3.

Compound 1 and netarsudil exhibited comparable disappearance rates over the course of this study attributable to esterase conversion of the prodrugs to the active metabolite and binding of the prodrugs to the corneal tissue. There was less binding of Compound 1 to the corneal tissue than netarsudil. In this study, generation of Compound 3 from Compound 1 far exceeded the amount of Compound 3 measured from netarsudil metabolism resulting in a near ten-fold higher Compound 3 formation rate from Compound 1 compared with netarsudil. The results indicate that following a 4-hour exposure of Compound 1 and netarsudil to cornea tissue, a higher amount of Compound 3 was available from Compound 1. The results also suggest that Compound 1 may have a lower propensity to sequester and depot in the cornea compared to netarsudil.

TABLE 5

Corneal Metabolism Analytical Data.

| Time (min) | Netarsudil (% of Initial) Mean ± SD | Compound 3 (% of Initial) Mean ± SD |
|---|---|---|
| 0 | 100.0 ± 0.0 | 0.0 ± 0.0 |
| 30 | 88.8 ± 0.1 | 0.0 ± 0.0 |
| 60 | 82.7 ± 7.5 | 0.3 ± 0.2 |
| 90 | 79.7 ± 4.7 | 0.6 ± 0.4 |
| 120 | 73.6 ± 2.7 | 0.8 ± 0.6 |
| 180 | 63.9 ± 3.3 | 2.2 ± 1.5 |
| 240 | 56.1 ± 5.2 | 3.7 ± 2.4 |
| Time (min) | Compound 1 (% of Initial) Mean ± SD | Compound 3 (% of Initial) Mean ± SD |
| 0 | 100.0 ± 0.0 | 1.5 ± 0.4 |
| 30 | 91.8 ± 8.6 | 3.5 ± 0.5 |
| 60 | 82.2 ± 0.6 | 6.8 ± 2.9 |
| 90 | 76.2 ± 3.5 | 12.3 ± 3.0 |
| 120 | 66.8 ± 6.1 | 18.7 ± 3.2 |
| 180 | 56.0 ± 3.2 | 29.9 ± 8.6 |
| 240 | 48.0 ± 3.0 | 45.4 ± 5.8 |

TABLE 6

Corneal Binding of Administered Compound.

| Time (min) | Compound 1 (% of Initial) Mean ± SD | Netarsudil (% of Initial) Mean ± SD |
|---|---|---|
| 240 | 25.4 ± 0.5 | 38.5 ± 6.7 |

TABLE 7

| Corneal Binding of Active Metabolite. | | |
| --- | --- | --- |
| Time (min) | Compound 3 (% of Initial Compound 1) Mean ± SD | Compound 3 (% of Initial Netarsudil) Mean ± SD |
| 240 | 3.6 ± 2.8 | 1.6 ± 0.6 |

Example 15: IOP or Hyperemia Effect of ROCK1 Compounds

Topical ophthalmic formulations are prepared according to Table 8, below. One drop (about 25-40 μL) of the formulation is instilled once daily in the evening to each affected eye of a subject(s) with open-angle glaucoma or ocular hypertension. After about 1, 2, or 3 or more consecutive days of administration, the subject(s) experiences: (1) an improvement in intraocular pressure (IOP) in the affected eye(s) as compared to the subject's baseline IOP prior to administration; (2) IOP reduction as compared to administration of netarsudil alone (0.02% weight/volume; Rhopressa®) or netarsudil/latanoprost fixed dose combination (0.02%/0.005% weight/volume; Rocklatan®); or (3) improvement insofar as one or more adverse reactions, as compared to administration of netarsudil alone (0.02% weight/volume; Rhopressa®) or netarsudil/latanoprost fixed dose combination (0.02%/0.005% weight/volume; Rocklatan®), are mitigated. For example, the subject(s) experiences a statistically significant (e.g., 95% CI) reduction of one or more of conjunctival hyperemia, instillation site pain, corneal *verticillata*, or conjunctival hemorrhage as compared to administration of netarsudil alone (0.02% weight/volume; Rhopressa®) or netarsudil/latanoprost fixed dose combination (0.02%/0.005% weight/volume; Rocklatan®). Rhopressa® prescribing information indicates a prevalence of conjunctival hyperemia of 53% and Rocklatan® prescribing information indicates a prevalence of conjunctival hyperemia of 59%.

Example 16: IOP and Hyperemia Effect of ROCK1 Compounds

A study was performed comparing formulations (A, B, and C) of 0.02% Compound 1 (in three salt forms: dimesylate, monomesylate, and dimesylate created in situ) with 0.005% Latanoprost following topical ocular administration to normotensive Dutch Belted (DB) rabbits were to evaluate the effects of each test article on: 1) Intraocular Pressure (IOP) and 2) the level of conjunctival hyperemia. Formulations A, B, and C were prepared and are described in Table 8.

TABLE 8

| Formulations of Compound 1 with Latanoprost. | | | |
| --- | --- | --- | --- |
| | Formulation A | Formulation B | Formulation C |
| Compound 1 monomesylate | 0.02% w/v [1] | | 0.02% w/v [1] |
| Compound 1 dimesylate | | 0.02% w/v [1] | |
| Latanoprost | 0.005% w/v | 0.005% w/v | 0.005% w/v |
| Boric Acid | 0.05% w/v | 0.05% w/v | 0.05% w/v |
| D-mannitol | 4.7% w/v | 4.7% w/v | 4.7% w/v |
| Benzalkonium Chloride (BAK) | 0.02% w/v | 0.02% w/v | 0.02% w/v |
| Methanesulfonic acid | | | 0.00397% w/v |
| pH | 5 | 5 | 5 |

[1] Based on the free base form (Compound 1).

All test articles were administered using a droptainer once daily in the morning. Test articles were dosed in the right eye (OD) while the left eye (OS) was not dosed but was used as a control for diurnal fluctuations in IOP. Animals in each group (7 male animals per group, no females) were dosed q.d. in the morning on Study Days 1-4. All treatments, about 140-150 μg/eye/day (about 36 μL), were administered via once daily eye drops (one drop per eye; test article instilled into the right eye (OD) at t=0 for each day) for four days. Following administration of the test articles, IOP measurements and images for hyperemia evaluation were collected at 2-, 4- and 8-hours post-dose for four consecutive days.

A single drop of proparacaine (0.5%) was applied to each eye prior to measuring IOP with a pneumotonometer (Reichert Model 30). IOP measurements were collected in triplicate for each eye at each time point. IOP was measured on Day 1, 2, 3 and 4 at time 0 (pre-dose) and at 2-, 4-, and 8-hours post-dose. IOP data were reported as the mean of the three measurements at each timepoint and as the difference in IOP between the treated (OD) and untreated (OS) eyes. The OS eyes served as a control for diurnal fluctuations in IOP. Hyperemia images were collected using a Samsung Phone S23 and scored for severity in a blinded manner. Severity scores were 0 (none), 1 (mild), 2 (moderate) and 3 (severe).

Each of the three formulations reduced IOP at all time points except 24-, 48-, and 72-hours post dose, and induced hyperemia. There was no difference between the three salt forms of test articles in either effect on IOP lowering or on hyperemia severity.

Example 17: IOP, Hyperemia, and Corneal Thinning Effect of ROCK1 Compounds

An 8-day study was performed to evaluate the effects on 1) Intraocular Pressure (IOP), 2) the level of conjunctival hyperemia, and 3) corneal thickness of topical ocular administration of Rhopressa, Formulation A, Formulation D, Formulation E, or Vehicle for Formulations A, D and E (see Table 9) to adult human subjects. All test articles were administered using a droptainer once daily in the morning on day 1 and then once daily in the evening on days 2-7. The mean change in diurnal mean IOP at day 8 is shown in Table 10. The data demonstrated that Formulations A, D and E were all within 1 mmHg of Rhopressa, which is generally not considered to be a clinically significant difference. Formulations A, D and E were also statistically significantly superior to vehicle.

TABLE 9

| Formulations of Compound 1 with Latanoprost. | | | |
| --- | --- | --- | --- |
| | Formulation A | Formulation D | Formulation E |
| Compound 1 monomesylate | 0.02% w/v [1] | 0.01% w/v [1] | 0.04% w/v [1] |
| Latanoprost | 0.005% w/v | 0.005% w/v | 0.005% w/v |
| Boric Acid | 0.05% w/v | 0.05% w/v | 0.05% w/v |
| D-mannitol | 4.7% w/v | 4.7% w/v | 4.7% w/v |
| Benzalkonium Chloride (BAK) | 0.02% w/v | 0.02% w/v | 0.02% w/v |
| pH | 5 | 5 | 5 |

[1] Based on the free base form (Compound 1).

TABLE 10

Mean change in diurnal mean IOP at Day 8.

| Day 8, Overall | Formulation D (0.01% Compound 1) | Formulation A (0.02% Compound 1) | Formulation E (0.04% Compound 1) | Vehicle | Rhopressa (0.02% netarsudil) |
|---|---|---|---|---|---|
| Mean ± SE [1] | −4.11 ± 0.71 | −4.99 ± 0.78 | −5.89 ± 0.42 | −1.46 ± 0.70 | −5.09 ± 0.59 |
| 90% CI [2] | (−5.28, −2.95) | (−6.28, −3.71) | (−5.89, −4.49) | (−2.62, −0.31) | (−6.06, −4.11) |
| LS Mean ± SE [1] | 19.11 ± 0.67 | 18.45 ± 0.66 | 17.98 ± 0.61 | 21.74 ± 0.65 | 17.14 ± 0.59 |
| Δ from Vehicle | −2.63 | −3.29 | −3.76 | — | −3.60 |
| SE of Δ | 0.93 | 0.93 | 0.89 | — | 0.88 |
| 90% CI [2] | (−4.45, −0.80) | (−5.10, −1.47) | (−5.50, −2.01) | — | (−5.32, −1.89) |

[1] Standard Error.
[2] Confidence Interval.

Figure 22:
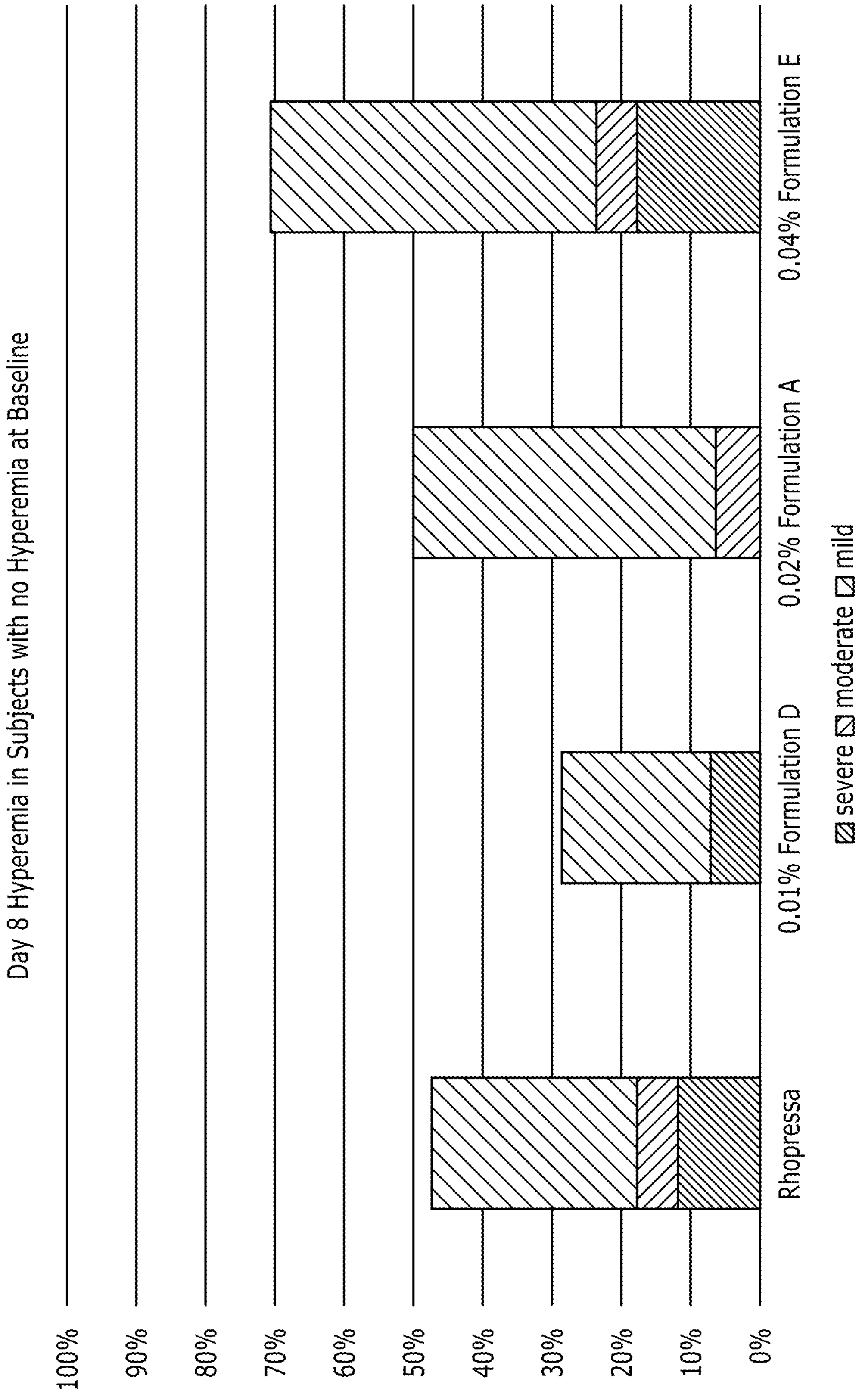
FIG. 22 depicts hyperemia levels at day 8 of treatment in subjects that had no hyperemia at baseline according to the study described in Example 17.

Regarding hyperemia, more subjects in the Formulation D arm of the study had no increase in hyperemia while on treatment than Formulation A, Formulation E, or Rhopressa arms of the study. Formulation D and Formulation A arms of the study produced a lower incidence and severity of hyperemia as compared to the Rhopressa arm of the study. Specifically, a 48% decrease in moderate to severe hyperemia was observed for the Formulation D arm as compared to the Rhopressa arm of the study, and a 38% decrease in moderate to severe hyperemia was observed for the Formulation A arm as compared to the Rhopressa arm of the study. An 8% increase in moderate to severe hyperemia was observed for the Formulation E arm as compared to the Rhopressa arm of the study. As assessed by biomicroscopy, for subjects with no hyperemia at baseline, Formulation D and Formulation A both achieved ≥50% reduction in incidence of moderate to severe hyperemia as compared to Rhopressa (see FIG. 22). Surprisingly, for subjects with no hyperemia at baseline, Formulation Formulation A achieved 100% reduction in incidence of severe hyperemia as compared to Rhopressa (see FIG. 22).

Regarding changes in corneal thickness while undergoing treatment, Table 11 shows a dose dependent decrease in central corneal thickness was observed, with the greatest decrease being observed in Rhopressa treated subjects.

TABLE 11

Change from screening in corneal thickness (μm) by visit in the study eye.

| Day 8, 8AM visit | Formulation D (0.01% Compound 1) | Formulation A (0.02% Compound 1) | Formulation F (0.02% Compound 1) | Vehicle | Rhopressa (0.02% netarsudil) |
|---|---|---|---|---|---|
| Mean ± SD [1] | −4.2 ± 11.79 | −5.8 ± 12.17 | −6.8 ± 12.24 | −1.9 ± 7.18 | −10.5 ± 14.83 |
| Median | −3.0 | −4.0 | −3.0 | 1.0 | −5.5 |
| Minimum | −23 | −25 | −34 | −9 | −50 |
| Maximum | 24 | 19 | 17 | 16 | 9 |

[1] Standard Deviation.

Example 18: IOP, Hyperemia, and Corneal Thinning Effect of ROCK1 Compounds

A 29-day study is performed to evaluate the effects on 1) Intraocular Pressure (IOP), 2) the level of conjunctival hyperemia, and 3) corneal thickness of topical ocular administration of Rocklatan, Latanoprost (0.005%), Formulation A, Formulation D, or Formulation F (see Table 11) to adult human subjects. All test articles were administered using a droptainer once daily in the morning for 29 consecutive days.

TABLE 11

Formulations of Compound 1 with Latanoprost.

| | Formulation A | Formulation D | Formulation F |
|---|---|---|---|
| Compound 1 monomesylate | 0.02% w/v [1] | 0.01% w/v [1] | 0.02% w/v [1] |
| Latanoprost | 0.005% w/v | 0.005% w/v | |
| Boric Acid | 0.05% w/v | 0.05% w/v | 0.05% w/v |
| D-mannitol | 4.7% w/v | 4.7% w/v | 4.7% w/v |
| Benzalkonium Chloride (BAK) | 0.02% w/v | 0.02% w/v | 0.02% w/v |
| pH | 5 | 5 | 5 |

[1] Based on the free base form (Compound 1).

Example 19: Safety Profile of ROCK1 Compounds

A 6-month study is performed to evaluate the safety of topical ocular administration of Formulation A or Formulation D (see Table 9), or Compound 1 monomesylate, once daily to canines. The formulations are observed to be clinically safe.

Example 20: IOP and Hyperemia Effect of ROCK1 Compounds

A 3-month study is performed to evaluate the effects on 1) Intraocular Pressure (IOP) and 2) the level of conjunctival hyperemia of topical ocular administration of Formulation A or Formulation D (see Table 9) once daily to rabbits (e.g., adult (about 9 months old) male Dutch belted rabbits; about 5-7 animals per group; OD eye dosed one drop (about 35 μL) once each morning between about 0600-0900 hours; OS eye used as control). The formulations are found to reduce IOP over the course of the study, and to mitigate hyperemia display (e.g., elicit less hyperemia severity per study group than a corresponding dosage regime of netarsudil dimesylate).

Example 21: Safety Profile of ROCK1 Compounds

A 6-month study is performed to evaluate the safety of topical ocular administration of Formulation A or Formulation D (see Table 9), or Compound 1 monomesylate, once daily to rabbits (e.g., adult (about 9 months old) male Dutch belted rabbits; about 5-7 animals per group; OD eye dosed one drop (about 35 μL) once each morning between about 0600-0900 hours; OS eye used as control). The formulations are observed to be clinically safe.

We claim:

1. A compound, having the formula:

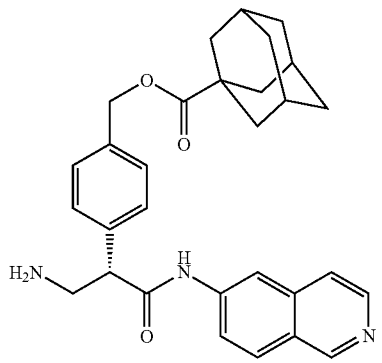 [SMILES: NC[C@@H](C(=O)Nc1ccc2cnccc2c1)c1ccc(COC(=O)C23CC4CC(CC(C4)C2)C3)cc1]

or a pharmaceutically acceptable salt thereof.

2. The compound of claim 1, which is a monomesylate salt of 4-((S)-3-amino-1-(isoquinolin-6-ylamino)-1-oxopropan-2-yl)benzyl adamantane-1-carboxylate.

3. The compound of claim 1, which is a dimesylate salt of 4-((S)-3-amino-1-(isoquinolin-6-ylamino)-1-oxopropan-2-yl)benzyl adamantane-1-carboxylate.

* * * * *